US010478409B2

(12) United States Patent
Cook et al.

(10) Patent No.: US 10,478,409 B2
(45) Date of Patent: *Nov. 19, 2019

(54) PHARMACEUTICAL COMPOSITIONS

(71) Applicant: KalVista Pharmaceuticals Limited, Salisbury (GB)

(72) Inventors: Gary Paul Cook, Westford, MA (US); Garry Thomas Gwozdz, Bethlehem, PA (US); Theodore Patrick Laslo, Bethlehem, PA (US)

(73) Assignee: Kalvista Pharmaceuticals Limited, Porton Down, England (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/715,930

(22) Filed: Sep. 26, 2017

(65) Prior Publication Data
US 2018/0021271 A1 Jan. 25, 2018

Related U.S. Application Data

(63) Continuation of application No. 14/655,435, filed as application No. PCT/GB2014/050052 on Jan. 9, 2014, now Pat. No. 9,849,100.

(60) Provisional application No. 61/750,568, filed on Jan. 9, 2013.

(30) Foreign Application Priority Data

Feb. 4, 2013 (GB) .................................. 1301895.7

(51) Int. Cl.
*A61K 9/00* (2006.01)
*A61K 31/00* (2006.01)
*A61K 45/00* (2006.01)
*A61K 47/00* (2006.01)
*A61K 31/165* (2006.01)
*A61K 31/455* (2006.01)
*A61K 31/42* (2006.01)
*A61K 31/445* (2006.01)
*A61K 9/14* (2006.01)
(Continued)

(52) U.S. Cl.
CPC .......... *A61K 31/165* (2013.01); *A61K 9/0019* (2013.01); *A61K 9/10* (2013.01); *A61K 9/14* (2013.01); *A61K 31/00* (2013.01); *A61K 31/166* (2013.01); *A61K 31/18* (2013.01); *A61K 31/198* (2013.01); *A61K 31/341* (2013.01); *A61K 31/381* (2013.01); *A61K 31/40* (2013.01); *A61K 31/404* (2013.01); *A61K 31/4025* (2013.01); *A61K 31/4045* (2013.01); *A61K 31/415* (2013.01); *A61K 31/42* (2013.01); *A61K 31/426* (2013.01); *A61K 31/427* (2013.01); *A61K 31/44* (2013.01); *A61K 31/4402* (2013.01); *A61K 31/4406* (2013.01); *A61K 31/445* (2013.01); *A61K 31/4406* (2013.01);
*A61K 31/4409* (2013.01); *A61K 31/4436* (2013.01); *A61K 31/455* (2013.01); *A61K 45/06* (2013.01); *A61K 47/26* (2013.01); *A61K 9/0051* (2013.01); *A61K 47/183* (2013.01)

(58) Field of Classification Search
CPC .... A61K 31/00; A61K 31/165; A61K 31/166; A61K 31/18; A61K 31/198; A61K 31/341; A61K 31/381; A61K 31/40; A61K 31/4025; A61K 31/404; A61K 31/4045; A61K 31/415; A61K 31/42; A61K 31/426; A61K 31/427; A61K 31/44; A61K 31/4402; A61K 31/4406; A61K 31/4409; A61K 31/4436; A61K 31/445; A61K 31/455; A61K 45/06; A61K 47/183; A61K 47/26; A61K 9/0019; A61K 9/0051; A61K 9/10; A61K 9/14

See application file for complete search history.

(56) References Cited

U.S. PATENT DOCUMENTS 5,187,157 A    2/1993  Kettner et al.
6,682,761 B2 * 1/2004  Pace ...................... A61K 9/145
                                                        264/5
(Continued)

FOREIGN PATENT DOCUMENTS

EP    0672658 A1    9/1995
EP    2281885 A1    2/2011
(Continued)

OTHER PUBLICATIONS

Khadka et al. "Pharmaceutical particle technologies: An approach to improve drug solubility, dissolution and bioavailability." Asian Journal of Pharmaceutical Sciences, 2014, 9:304-316 (Year: 2014).*
(Continued)

*Primary Examiner* — Robert A Wax
*Assistant Examiner* — Olga V. Tcherkasskaya
(74) *Attorney, Agent, or Firm* — BakerHostetler

(57) ABSTRACT

The invention relates to aqueous suspension pharmaceutical compositions of poorly water soluble drugs, wherein said drugs are selected from compounds of formula I

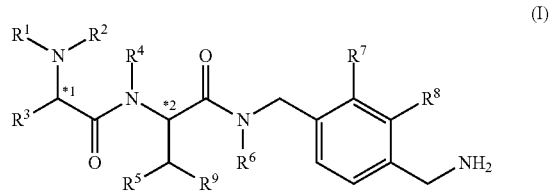

(I)

wherein $R^1$-$R^9$ are defined herein; processes for preparing these compositions and their use in medicine, especially their use in the treatment of ocular diseases.

32 Claims, 4 Drawing Sheets

(51) Int. Cl.
| | |
|---|---|
| A61K 47/26 | (2006.01) |
| A61K 9/10 | (2006.01) |
| A61K 45/06 | (2006.01) |
| A61K 31/166 | (2006.01) |
| A61K 31/18 | (2006.01) |
| A61K 31/198 | (2006.01) |
| A61K 31/341 | (2006.01) |
| A61K 31/381 | (2006.01) |
| A61K 31/40 | (2006.01) |
| A61K 31/4025 | (2006.01) |
| A61K 31/404 | (2006.01) |
| A61K 31/4045 | (2006.01) |
| A61K 31/415 | (2006.01) |
| A61K 31/426 | (2006.01) |
| A61K 31/427 | (2006.01) |
| A61K 31/44 | (2006.01) |
| A61K 31/4402 | (2006.01) |
| A61K 31/4406 | (2006.01) |
| A61K 31/4409 | (2006.01) |
| A61K 31/4436 | (2006.01) |
| A61K 47/18 | (2017.01) |

(56) References Cited

U.S. PATENT DOCUMENTS

| | | | |
|---|---|---|---|
| 2002/0012704 A1 | 1/2002 | Pace et al. | |
| 2002/0058065 A1* | 5/2002 | Guivarc'h | A61K 9/145 424/465 |
| 2006/0148901 A1 | 7/2006 | Sturzebecher et al. | |
| 2013/0058965 A1* | 3/2013 | Ferguson | A61K 9/0019 424/185.1 |
| 2015/0191421 A1* | 7/2015 | Northen | C07C 237/22 514/616 |

FOREIGN PATENT DOCUMENTS

| | | | |
|---|---|---|---|
| JP | 2009529553 A | 8/2009 | |
| WO | WO92004371 | 3/1992 | |
| WO | WO94029335 | 12/1994 | |
| WO | WO95007921 | 3/1995 | |
| WO | WO02044145 | 6/2002 | |
| WO | WO03076458 A2 | 9/2003 | |
| WO | WO2004062657 A1 | 7/2004 | |
| WO | WO2005123680 A1 | 12/2005 | |
| WO | WO2007104541 A2 | 9/2007 | |
| WO | WO2008016883 A2 | 2/2008 | |
| WO | WO2008049595 A1 | 5/2008 | |
| WO | WO2011051671 A1 | 5/2011 | |
| WO | WO2011080148 A2 | 7/2011 | |
| WO | WO2011094496 A2 | 8/2011 | |
| WO | WO2011118672 A1 | 9/2011 | |
| WO | WO2012004678 A2 | 1/2012 | |
| WO | WO2012017020 A1 | 2/2012 | |
| WO | WO2013005045 A1 | 1/2013 | |
| WO | WO-2013005045 A1 * | 1/2013 | C07C 237/22 |
| WO | WO2014006414 A1 | 1/2014 | |

OTHER PUBLICATIONS

Patel et al. An overview of size reduction technologies in the field of pharmaceutical manufacturing. Asian Journal of Pharmaceutical Sciences. Oct.-Dec. 2008:216-220. (Year: 2008).*

Savjani et al. "Drug Solubility: Importance and Enhancement Techniques". ISRN Pharm. vol. 2012, article ID 195727, 10 pages. (Year: 2012).*

Bhoola et al., "Bioregulation of Kinins: Kallikreins, Kininogens and Kininases", Pharmacological Rev., 1992, 44(1), 1-80.

Campbell, "Towards Understanding the Kallikrein-Kinin System: Insights from the Measurement of Kinin Peptides", Brazilian Journal of Medical and Biological Research, 2000, 33(6), 665-677.

Chilcote et al., "ASP-634: An Oral Drug Candidate for Diabetic Macular Edema", ARVO, Mar. 2012, Presentation 2240, Abstract, 1 page.

Clermont et al., "Plasma Kallikrein Mediates Retinal Vascular Dysfunction and Induces Retinal Thickening in Diabetic Rats", Diabetes, May 2011, 60(5), 1590-98.

Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, 1064-1077.

Evans et al., "Selective Inhibitors of Plasma Kallikrein", Immunopharmacology, May 1996, 32(1-3), 115-116.

Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.

Griesbacher et al., "Involvement of Tissue Kallikrein But Not Plasma Kallikrein in the Development of Symptoms Mediated by Endogenous Kinins in Acute Pancreatitis in Rats", British Journal of Pharmacology, 2002, 137, 692-700.

Kolte et al., "Biochemical Characterization of a Novel High-Affinity and Specific Kallikrein Inhibitor", British Journal of Pharmacology, 2011, 162, 1639-1649.

Lehmann, "Ecallantide (DX-88), A Plasma Kallikrein Inhibitor for the Treatment of Hereditary Angioedema and the Prevention of Blood Loss in On-Pump Cardiothoracic Surgery", Expert Opinion on Biological Therapy, Jul. 2008, 8(8), 1187-1199.

Leinweber et al, "Possible Physiological Roles of Carboxylic Ester Hydrolases", Drug Metabolism Reviews, 1987, 18 (4), 379-439.

Marceau et al., "Bradykinin Receptor Ligands: Therapeutic Perspectives", Nature Reviews Drug Discovery, Oct. 2004, 3, 845-852.

Okada et al.; "Development of Potent and Selective Plasmin and Plasma Kallikrein Inhibitors and Studies on the Structure-Activity Relationship", Chem. Pharm. Bull., Sep. 2000, 48(12), 1964-1972.

Stahl, "A Handbook of Pharmaceutical Salts: Properties, Selection and Use", Wiley-VCH, Weinheim, Germany, 2002, 24(3), 1 page.

Stegemann et al., "When Poor Solubility Becomes an Issue: From Early Stage to Proof of Concept", European Journal of Pharmaceutical Sciences, 2007, 31, 249-261.

Teno et al., "Development of Active Center-Directed Plasmin and Plasma Kallikrein Inhibitors and Studies on the Structure-Inhibitory Activity Relationship", Chemical and Pharmaceutical Bulletin, 1993, 41(6), 1079-1090.

Wermuth, "The Practice of Medicinal Chemistry", 2003, 2nd Ed., 561-585.

Young et al., "Small Molecule Inhibitors of Plasma Kallikrein", Bioorganic & Medicinal Chemistry Letters, Apr. 2006, 16 (7), 2034-2036.

Zhang et al., "Discovery of Highly Potent Small Molecule Kallikrein Inhibitors"; Medicinal Chemistry, Nov. 2006, 2 (6), 545-553.

* cited by examiner

PHARMACEUTICAL COMPOSITIONS

CROSS-REFERENCE TO RELATED APPLICATIONS

This application is a continuation of U.S. patent application Ser. No. 14/655,435, filed Jun. 25, 2015, which is the National Stage of International Patent Application No. PCT/GB2014/050052 filed Jan. 9, 2014, which claims the benefit of U.S. Provisional Patent Application No. 61/750,568, filed Jan. 9, 2013; and Great Britain Patent Application No. 1301895.7, filed Feb. 4, 2013, the disclosures of which are incorporated herein by reference in their entireties.

TECHNICAL FIELD

The invention relates to aqueous suspension pharmaceutical compositions of poorly water soluble drugs, processes for preparing these compositions and their use in medicine, especially their use in the treatment of ocular diseases.

BACKGROUND OF THE INVENTION

Plasma kallikrein is a trypsin-like serine protease that can liberate kinins from kininogens (K. D. Bhoola et al., "Kallikrein-Kinin Cascade", *Encyclopedia of Respiratory Medicine*, 483-493; J. W. Bryant et al., "Human plasma kallikrein-kinin system: physiological and biochemical parameters" *Cardiovascular and haematological agents in medicinal chemistry*, 7, 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade, although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists, for example icatibant) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE), which results in intermittent swelling of face, hands, throat, gastro-intestinal tract and genitals. Blisters formed during acute episodes contain high levels of plasma kallikrein which cleaves high molecular weight kininogen liberating bradykinin, thereby leading to increased vascular permeability. Treatment with a large protein plasma kallikrein inhibitor has been shown to treat HAE effectively by preventing the release of bradykinin, which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, 1187-99).

The plasma kallikrein-kinin system is a system of blood proteins that plays a role in inflammation, blood pressure control, coagulation and pain. The plasma kallikrein-kinin system is abnormally abundant in patients with advanced diabetic macular oedema. It has recently been discovered that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, 1590-98). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular oedema. Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described, for example by Garrett et al. ("Peptide aldehyde . . . " *J. Peptide Res.* 52, 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, 1929-34 (1994)), Kettner et al. (U.S. Pat. No. 5,187,157), N. Teno et al. (*Chem. Pharm. Bull.* 41, 1079-1090 (1993)), W. B. Young et al. ("Small molecule inhibitors of plasma kallikrein" *Bioorg. Med. Chem. Letts.* 16, 2034-2036 (2006)), Okada et al. ("Development of potent and selective plasmin and plasma kallikrein inhibitors and studies on the structure-activity relationship" *Chem. Pharm. Bull.* 48, 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, 545-553 (2006)), Sinha et al. ("Inhibitors of plasma kallikrein" WO08/016883), Evans et al. ("Benzylamine derivatives as inhibitors of plasma kallikrein" WO2013/005045), Brandl et al. ("N-((6-amino-pyridin-3-yl)methyl)-heteroaryl-carboxamides as inhibitors of plasma kallikrein" WO2012/017020), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, the only selective plasma kallikrein inhibitor approved for medical use is Ecallantide. Ecallantide is formulated as a solution for injection. It is a large protein plasma kallikrein inhibitor that presents a risk of anaphylactic reactions. Other plasma kallikrein inhibitors known in the art are generally small molecules that usually include highly polar and ionisable functional groups, such as guanidines or amidines. It is well known that such functional groups impart a high degree of aqueous solubility to the compound. However, it is also well known that highly polar and ionisable guanidine or amidine functionalities may be limiting to gut permeability and therefore to oral availability (see, for example, "Small Molecule Anticoagulant/Antithrombotic Agents" *Annual Reports in Medicinal Chemistry*, Volume 40, 2005, Pages 85-101 Robert M. Scarborough, Anj ali Pandey, Xiaoming Zhang and Tamie J. Chilcote and Sukanto Sinha, "ASP-634: An Oral Drug Candidate for Diabetic Macular Edema", ARVO 2012 May 6-May 9, 2012, Fort Lauderdale, Fla., Presentation 2240). It is further reported that oral absorption may be improved by creating a prodrug such as ASP-634. However, it is well known that prodrugs can suffer from several drawbacks, for example, poor chemical stability and potential toxicity from the inert carrier or from unexpected metabolites.

Ionisable functional groups provide water solubility but, as a rule, water soluble small molecules are rapidly cleared, for example from the vitreous (see "Review: Practical Issues in Intravitreal Drug Delivery", *Journal of Ocular Pharmacology and Therapeutics*, Volume 17, Number 4, 2001, page 393-401, David Maurice). Also, solubilised drugs are susceptible to degradation. It is an aim of the present invention to identify compounds that lack polar or ionisable groups, for example compounds with a pKa less than 11, which are sparingly soluble, and that would enable formulation of serine protease inhibitors as aqueous suspensions thus providing extended duration of the exposure and an extended shelf life.

There are only few reports of plasma kallikrein inhibitors that do not feature guanidine or amidine functionalities. For example Brandl et al. ("N-((6-amino-pyridin-3-yl)methyl)-heteroaryl-carboxamides as inhibitors of plasma kallikrein" WO2012/017020) and Evans et al. ("Benzylamine derivatives as inhibitors of plasma kallikrein" WO2013/005045). Brandl discloses plasma kallikrein inhibitors that include an amino-pyridine functionality. Oral efficacy in a rat model is demonstrated for one example at relatively high doses of 30 mg/kg and 100 mg/kg but the pharmacokinetic profile is not reported. Thus it is not yet known whether such compounds will provide sufficient oral availability for progression to the clinic. Evans discloses plasma kallikrein inhibitors that feature a benzylamine functionality. Pharmacokinetic data is presented for one example following intravitreous administration to rabbits. However, the disclosed data is limited to only 7 days post dosing; no data past this time point is described. Evans further discloses thermodynamic solubility data that demonstrate that the inhibitors are very slightly soluble, practically insoluble or insoluble (less than 1 mg/mL in phosphate buffer).

Intravenous administration of drugs is known in the art, and is particularly useful in treating life threatening conditions in view of the almost immediate effect on a subject following administration. However, there is a risk that intravenous administration of compositions that contain drugs that are poorly soluble in water may effect precipitation in vivo, which could cause serious adverse side-effects or death. The use of stabilizing agents to mitigate the risk of precipitation is known in the art. However, the amount of stabilizing agent may need to be excessive in compositions that contain poorly soluble drugs thus causing adverse side-effects, and so their use is suboptimal. There is therefore a need for compositions which can be administered safely without the risk of serious adverse side-effects.

Triesence® is a suspension of triamcinolone, a corticosteroid, for intravitreal injection. Triesence® is indicated for the treatment of ophthalmic diseases: sympathetic ophthalmia, temporal arteritis, uveitis, and ocular inflammatory conditions unresponsive to topical corticosteroids. However, the complexity of ophthalmic disorders suggests there is a need for pharmacologic agents with modes of action distinguishable from corticosteroids. Plasma kallikrein inhibitors could fulfil this need.

It is an object of the present invention to provide a composition of a poorly soluble plasma kallikrein inhibitor that may be administered parenterally. In the present application, the aforesaid plasma kallikrein inhibitor hereinafter refers to a compound of formula I as defined below.

Intravitreal administration of the compositions of the present invention results in slow elimination of the active ingredient from the vitreous humor. Moreover, high concentrations of the active ingredient in the retina (with choroid) are observed, which confirms that the active ingredient reaches the posterior ocular tissues.

It is therefore a further object of the invention to provide a composition with improved patient compliance, by reducing the frequency at which the composition needs to be administered to a subject.

SUMMARY OF THE INVENTION

The present invention relates to an aqueous suspension pharmaceutical composition for parenteral administration comprising a very slightly soluble, practically insoluble or insoluble active ingredient that is a plasma kallikrein inhibitor of formula I.

The present invention further relates to processes for preparing pharmaceutical compositions of the invention comprising:

(i) providing an active ingredient that is a plasma kallikrein inhibitor of formula I, or a pharmaceutically acceptable salt thereof;

(ii) providing an aqueous vehicle, wherein the aqueous vehicle optionally comprises a stabilising agent and/or a tonicity agent, and optionally one or more pharmaceutically acceptable excipients; and (iii) suspending the active ingredient, or the pharmaceutically acceptable salt thereof in the aqueous vehicle obtained in step (ii).

In an embodiment, the process of the invention may further comprise the step of reducing the particle size of the active ingredient. In some embodiments, the particle size of the active ingredient may be reduced when the active ingredient is suspended in the aqueous vehicle. In this embodiment, suitable methods of reducing the particle size of the active ingredient include precipitation processes, processes using wet ball milling such as bead milling or pearl milling, or processes using high pressure homogenisation. Alternatively, the particle size of the active ingredient may be reduced using high shear fluid processing (for example by use of Microfluidics high shear fluid processor). In other embodiments, the method of reducing the particle size of the active ingredient may occur in the dry form prior to its suspension in the aqueous vehicle. Examples of methods of reducing the particle size of an active ingredient in dry form include ball milling, jet milling and roller milling. Such methodologies are known in the art, see "Pharmaceutical Preformulation and Formulation" Ed. Mark Gibson, Informa Healthcare, New York, 2009, Chapter 6 "Preformulation as an Aid to Product Design in Early Drug Development", "Pharmaceutical nanocrystals" Wang G. D. et al Current Opinion in Chemical Engineering Volume 1 issue 2 pages 102-107 and "Drug nanocrystals for the formulation of poorly soluble drugs and its application as a potential drug delivery system" Gao L. et al J Nanopart Res 2008; 10:845-862. Microfluidization processors are available from Microfluidics, 90 Glacier Drive Suite 1000, Westwood, Mass. 02090 USA.

The present invention further relates to methods for treating a disease or condition mediated by plasma kallikrein comprising parenteral administration of a pharmaceutical composition of the invention to a mammal.

DETAILED DESCRIPTION OF THE INVENTION

Active Ingredient

Figure 1:
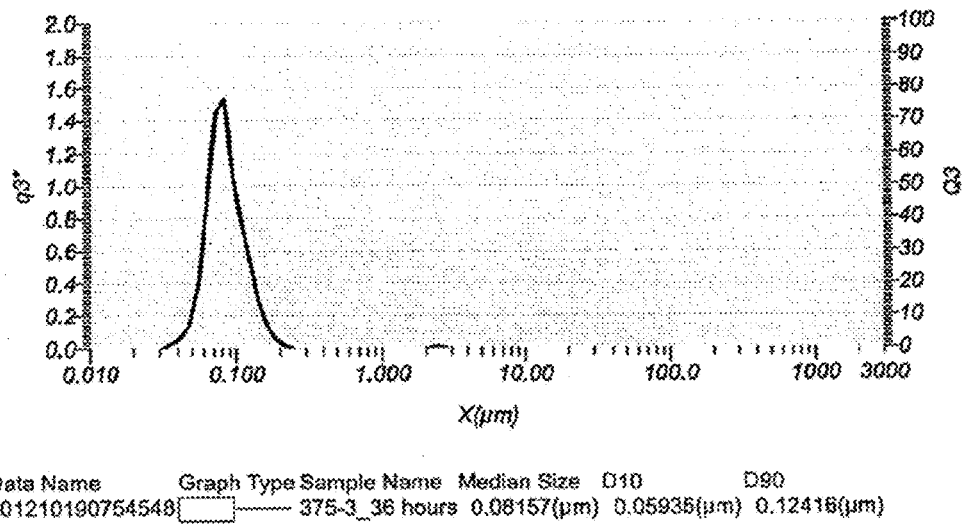
FIG. 1 shows the results of laser diffraction particle-size measurements carried out on a suspension according to the present invention.

The present compositions are aqueous dosage forms for parenteral administration. Such dosage forms may be preferable to solid dosage forms for oral administration in view of the relatively poor gut permeability and oral availability of typical protease inhibitors.

The compositions of the invention are aqueous suspensions, i.e. they contain suspended active ingredient. However, the compositions may also include dissolved active ingredient. The amount of dissolved active ingredient may vary from less than 0.01% to about 3% by weight of the total amount of active ingredient in the composition. Typically, about 0.01% to about 0.3% of the total active ingredient is dissolved within the composition. For example, the compositions may be saturated or supersaturated.

In some embodiments, the compositions of the invention include crystalline active ingredient. The use of crystalline active ingredient has been found to lengthen the dissolution time compared to the use of amorphous (non-crystalline) active ingredient, which may be preferred where relatively infrequent administration of composition to a subject is desirable.

In some embodiments, the compositions of the invention include amorphous (non-crystalline) active ingredient. The use of amorphous active ingredient has been found to result in more rapid dissolution of active ingredient compared to the use of crystalline active ingredient, which may be desirable in some embodiments, for example where it is desirable for the drug to enter the bloodstream quickly.

The compositions can include a mixture of amorphous and crystalline active ingredient.

The compositions of the invention have a relatively long period of action, because the use of suspensions of poorly soluble compounds means that the compounds have relatively long dissolution times. This is beneficial in terms of patient compliance, because it means that the compositions can be administered less frequently than would otherwise have been necessary whilst still maintaining sufficient levels of drug in vivo to provide the intended clinical effect.

The compositions of the invention are aqueous, but can be pre-formulated as a sterile, non-aqueous solution or in a dried form which can be subsequently reconstituted with a suitable aqueous vehicle (e.g. sterile, pyrogen-free water).

In one embodiment, the composition includes particles of active ingredient which have an average (D50) size of from about 10 nm to about 100 µm. For example, the composition may include particles of active ingredient which have an average (D50) size of from about 500 nm to about 100 µm, such as from about 1 µm to about 100 µm. The composition may include particles of active ingredient which have an average (D50) size of from about 10 nm to about 1000 nm, such as from about 10 nm to about 500 nm.

The compositions may include nanosuspensions of active ingredient. Nanosuspensions of poorly soluble drugs are described in Homar et al., "An Aqueous Intravenous Nanosuspension with Reduced Adverse Effects", WO 2011/080148, also Wang et al., "Pharmaceutical nanocrystals", Current Opinion in Chemical Engineering, Volume 1, Issue 2, May 2012, Pages 102-107 and "Drug nanocrystals for the formulation of poorly soluble drugs and its application as a potential drug delivery system" Gao L. et al J Nanopart Res 2008; 10:845-862. The use of nanosuspensions has been found to reduce the amount of stabilizing agent that is needed to prevent undesirable agglomeration of particles of active ingredient. The use of nanosuspensions may eliminate the need to use any stabilizing agent.

Typically, a nanosuspension includes particles of active ingredient having an average (D50) size of from about 10 nm to about 1000 nm. For example, the nanosuspension may include particles of active ingredient having an average size of 10 nm, 20 nm, 30 nm, 40 nm, 50 nm, 100 nm, 250 nm, 500 nm, 750 nm or 1000 nm.

The compositions of the invention may be hypotonic, isotonic or hypertonic and typically have an osmolality of from about 250 to about 350 mOsmol/kg. For example, the compositions may have an osmolality of 250, 260, 270, 280, 290, 300, 310, 320, 330, 340 or 350 mOsmol/kg.

The compositions will typically be at a pH of from about 2 to about 10, e.g. pH 2, 3, 4, 5, 6, 7, 8, 9 or 10. Preferably, the compositions will be at a pH of from about 4 to about 8.

The composition of the invention includes a plasma kallikrein inhibitor of formula I as active ingredient. Typically, the composition includes an active ingredient in an amount of from about 0.001% to about 10% by weight of the composition. The composition may include active ingredient in an amount of about 0.01%, 0.03%, 0.05%, 0.07%, 0.1%, 0.25%, 0.5%, 1.0%, 2.0%, 3.0%, 4.0%, 5.0%, 6.0%, 7.0%, 8.0%, 9.0% or 10.0%. In certain preferred embodiments, the composition includes an active ingredient in an amount of from about 0.01% to about 0.1% by weight of the composition, such as from about 0.01% to about 0.03% by weight of the composition.

In some embodiments the composition may be provided as a bulk suspension which is further diluted, for example with sterile, pyrogen-free water, prior to use.

The active ingredient is a plasma kallikrein inhibitor of formula I

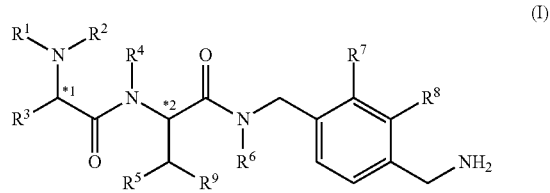
(I)

wherein:

$R^1$ is selected from H, alkyl, —COalkyl, —COaryl, —COheteroaryl, —CO$_2$alkyl, —(CH$_2$)$_a$OH, —(CH$_2$)$_b$COOR$^{10}$, —(CH$_2$)$_c$CONH$_2$, —SO$_2$alkyl and —SO$_2$aryl;

$R^2$ is selected from H and alkyl;

$R^3$ is selected from H, alkyl, —(CH$_2$)$_d$aryl, —(CH$_2$)$_e$heteroaryl, —(CH$_2$)$_f$cycloalkyl, —(CH$_2$)$_g$heterocycloalkyl, —CH(cycloalkyl)$_2$ and —CH(heterocycloalkyl)$_2$;

$R^4$ and $R^6$ are independently selected from H and alkyl;

$R^5$ is selected from H, alkyl, alkoxy and OH;

or $R^4$ and $R^5$, together with the atoms to which they are attached, may join to form a 5- or 6-membered azacycloalkyl structure;

$R^7$ and $R^8$ are independently selected from H, alkyl, alkoxy, CN and halo;

$R^9$ is aryl or heteroaryl;

$R^{10}$ is H or alkyl;

a, b, c, d, e, f and g are independently 1, 2 or 3;

*1 and *2 denote chiral centres;

alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be substituted with 1 or 2 substituents independently selected from (C$_3$-C$_{10}$)cycloalkyl, (C$_1$-C$_6$)alkoxy, OH, CN, CF$_3$, COOR$^{11}$, fluoro and NR$^{11}$R$^{12}$;

cycloalkyl is a mono- or bi-cyclic saturated hydrocarbon of between 3 and 10 carbon atoms; cycloalkyl may optionally be fused to an aryl group;

heterocycloalkyl is a C-linked or N-linked 3 to 10 membered saturated, mono- or bi-cyclic ring, wherein said heterocycloalkyl ring contains, where possible, 1, 2 or 3 heteroatoms independently selected from N, NR$^{11}$ and O;

alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from (C$_3$-C$_{10}$)cycloalkyl, OH, CN, CF$_3$, COOR$^{11}$, fluoro and NR$^{11}$R$^{12}$;

aryl is phenyl, biphenyl or naphthyl; aryl may be optionally substituted with up to 5 substituents independently selected from alkyl, alkoxy, OH, halo, CN, COOR$^{11}$, CF$_3$ and NR$^{11}$R$^{12}$;

heteroaryl is a 5, 6, 9 or 10 membered mono- or bi-cyclic aromatic ring, containing, where possible, 1, 2 or 3 ring members independently selected from N, NR$^{11}$, S and O; heteroaryl may be optionally substituted with 1, 2 or 3 substituents independently selected from alkyl, alkoxy, OH, halo, CN, COOR$^{11}$, CF$_3$ and NR$^{11}$R$^{12}$;

$R^{11}$ and $R^{12}$ are independently selected from H and alkyl;

and tautomers, isomers, stereoisomers (including enantiomers, diastereoisomers and racemic and scalemic mixtures thereof), pharmaceutically acceptable salts and solvates thereof.

In some embodiments, the protease inhibitor is a compound of formula I wherein:

$R^1$ is selected from H, alkyl, —COalkyl, —COaryl, —CO$_2$alkyl, —CH$_2$CH$_2$OH, —CH$_2$COOR$^{10}$, —CH$_2$CONH$_2$, —SO$_2$alkyl and —SO$_2$aryl;

$R^2$ is selected from H and alkyl;

$R^3$ is selected from alkyl, —CH$_2$aryl, —CH$_2$cycloalkyl and —CH(cycloalkyl)$_2$;

$R^4$ and $R^6$ are independently selected from H and alkyl;

$R^5$ is selected from H, alkyl, and OH;

or $R^4$ and $R^5$, together with the atoms to which they are attached, may join to form a 5- or 6-membered azacycloalkyl structure;

$R^7$ and $R^8$ are independently selected from H, F, and Cl;

$R^9$ is aryl;

$R^{10}$ is H or alkyl;

*1 and *2 denote chiral centres;

alkyl is a linear saturated hydrocarbon having up to 6 carbon atoms (C$_1$-C$_6$) or a branched saturated hydrocarbon of between 3 and 6 carbon atoms (C$_3$-C$_6$); alkyl may optionally be substituted with 1 or 2 substituents independently selected from (C$_3$-C$_{10}$)cycloalkyl, (C$_1$-C$_6$)alkoxy, OH, CN, CF$_3$, COOR$^{11}$, fluoro and NR$^{11}$R$^{12}$;

cycloalkyl is a mono- or bi-cyclic saturated hydrocarbon of between 3 and 10 carbon atoms;

alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from (C$_3$-C$_{10}$)cycloalkyl, OH, CN, CF$_3$, COOR$^{11}$, fluoro and NR$^{11}$R$^{12}$;

aryl is phenyl, biphenyl or naphthyl; aryl may be optionally substituted with up to 5 substituents independently selected from alkyl, alkoxy, OH, halo, CN, COOR$^{11}$, CF$_3$ and NR$^{11}$R$^{12}$;

$R^{11}$ and $R^{12}$ are independently selected from H and alkyl;

and tautomers, isomers, stereoisomers (including enantiomers, diastereoisomers and racemic and scalemic mixtures thereof), pharmaceutically acceptable salts and solvates thereof.

In preferred embodiments, the active ingredient is a compound selected from:

(S)—N-(4-Aminomethyl-benzyl)-2-[(R)-3-(4-ethoxy-phenyl)-2-propionylamino-propionylamino]-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-benzamide;

{(R)-1-[(S)-1-(4-Aminomethyl-benzylcarbamoyl)-2-phenyl-ethylcarbamoyl]-2-cyclohexyl-ethylamino}-acetic acid;

(S)—N-(4-Aminomethyl-3-fluoro-benzyl)-2-[(R)-3-(4-ethoxy-phenyl)-2-propionylamino-propionylamino]-3-phenyl-propionamide;

(S)—N-(4-Aminomethyl-2-chloro-benzyl)-2-[(R)-3-(4-ethoxy-phenyl)-2-propionylamino-propionylamino]-3-phenyl-propionamide;

(S)—N-(4-Aminomethyl-benzyl)-3-(3,4-dichloro-phenyl)-2-[(R)-3-(4-ethoxy-phenyl)-2-propionylamino-propionylamino]-propionamide;

(S)—N-(4-Aminomethyl-3-chloro-benzyl)-2-[(R)-3-(4-ethoxy-phenyl)-2-propionylamino-propionyl amino]-3-phenyl-propionamide;

(S)—N-(4-Aminomethyl-benzyl)-2-{[(R)-3-(4-ethoxy-phenyl)-2-propionylamino-propionyl]-methyl-amino}-3-phenyl-propionamide;

({(R)-1-[(S)-1-(4-Aminomethyl-benzylcarbamoyl)-2-phenyl-ethylcarbamoyl]-2-cyclohexyl-ethyl}-methyl-amino)-acetic acid;

(S)—N-(4-Aminomethyl-3-fluoro-benzyl)-2-{[(R)-3-(4-ethoxy-phenyl)-2-propionylamino-propionyl]-methyl-amino}-3-phenyl-propionamide;

N—[(R)-1-{[(S)-1-(4-Aminomethyl-benzylcarbamoyl)-2-phenyl-ethyl]-methyl-carbamoyl}-2-(4-ethoxy-phenyl)-ethyl]-benzamide;

N—[(R)-1-{[(S)-1-(4-Aminomethyl-benzylcarbamoyl)-2-phenyl-ethyl]-methyl-carbamoyl}-2-(4-ethoxy-phenyl)-ethyl]-isobutyramide;

N aphthalene-1-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;

(R)-2-Amino-N-[(1S,2S)-1-(4-aminomethyl-benzylcarbamoyl)-2-hydroxy-2-phenyl-ethyl]-3-(4-ethoxy-phenyl)-propionamide;

N—[(R)-1-[(S)-1-(4-Aminomethyl-benzylcarbamoyl)-2-phenyl-ethylcarbamoyl]-2-(4-ethoxy-phenyl)-ethyl]-nicotinamide;

(2S,3S)—N-(4-Aminomethyl-benzyl)-2-[(R)-3-(4-ethoxy-phenyl)-2-propionylamino-propionylamino]-3-hydroxy-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-isonicotinamide;

Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;

Thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Cyclohexanecarboxylic acid [(R)-1-[(S)-1-(4-aminomethyl-benzylcarbamoyl)-2-phenyl-ethylcarbamoyl]-2-(4-ethoxy-phenyl)-ethyl]-amide;

Isoxazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Pyridine-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Benzo[b]thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

(R)—N—[(S)-1-(4-Aminomethyl-benzylcarbamoyl)-2-phenyl-ethyl]-2-(4-chloro-benzenesulfonylamino)-3-(4-ethoxy-phenyl)-propionamide;

N—[(R)-1-[(S)-1-(4-Aminomethyl-benzylcarbamoyl)-2-phenyl-ethylcarbamoyl]-2-(4-ethoxy-phenyl)-ethyl]-3-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2-chloro-benzamide N—[(R)-1-[(S)-1-(4-Aminomethyl-benzylcarbamoyl)-2-phenyl-ethylcarbamoyl]-2-(4-ethoxy-phenyl)-ethyl]-3-trifluoromethyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide;

(S)—N-(4-Aminomethyl-benzyl)-2-[(R)-3-(4-ethoxy-phenyl)-2-(2-phenyl acetylamino-acetylamino)-propionylamino]-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide;

N—[(R)-1-[(S)-1-(4-Aminomethyl-benzylcarbamoyl)-2-phenyl-ethylcarbamoyl]-2-(4-ethoxy-phenyl)-ethyl]-6-methyl-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2-methyl-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2,6-dichloro-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-5,6-dichloro-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2,3,6-trifluoro-isonicotinamide;

N—[(R)-1-[(S)-1-(4-Aminomethyl-benzylcarbamoyl)-2-phenyl-ethylcarbamoyl]-2-(4-ethoxy-phenyl)-ethyl]-3,3,3-trifluoro-propionamide;

2,4-Dimethyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

2-Methyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Chloro-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

4-Methyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

Furan-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Methyl-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-2-methoxy-isonicotinamide;

3-Methyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Amino-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-propoxy-phenyl)-ethyl]-benzamide;

N—[(R)-1-[(S)-1-(4-Aminomethyl-benzylcarbamoyl)-2-pyridin-2-yl-ethylcarbamoyl]-2-(4-ethoxy-phenyl)-ethyl]-benzamide;

N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-(4-chloro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-pyridin-3-yl-ethylcarbamoyl]-2-(4-ethoxy-phenyl)-ethyl]-benzamide;

N—[(R)-1-[(S)-1-(4-Aminomethyl-benzylcarbamoyl)-2-(4-methoxy-phenyl)-ethylcarbamoyl]-2-(4-ethoxy-phenyl)-ethyl]-benzamide;
N—[(R)-1-[(S)-1-(4-Aminomethyl-benzylcarbamoyl)-2-pyridin-4-yl-ethylcarbamoyl]-2-(4-ethoxy-phenyl)-ethyl]-benzamide;
N—[(R)-1-[(S)-1-(4-Aminomethyl-benzylcarbamoyl)-2-(3-fluoro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-thiophen-2-yl-ethylcarbamoyl]-2-(4-ethoxy-phenyl)-ethyl]-benzamide;
N—[(R)-1-[(S)-1-(4-Aminomethyl-benzylcarbamoyl)-2-thiophen-3-yl-ethylcarbamoyl-2-(4-ethoxy-phenyl)-ethyl]-benzamide;
N—[(R)-1-[(S)-1-(4-Aminomethyl-benzylcarbamoyl)-2-thiazol-4-yl-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide;
N—[(R)-1-[(S)-1-(4-Aminomethyl-3-chloro-benzylcarbamoyl)-2-phenyl-ethylcarbamoyl]-2-(4-ethoxy-phenyl)-ethyl]-benzamide;
Pyridine-2-carboxylic acid [(R)-1-[(S)-1-(4-aminomethyl-benzylcarbamoyl)-2-thiophen-2-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide;
Pyridine-2-carboxylic acid [(R)-1-[(S)-1-(4-aminomethyl-3-chloro-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-isonicotinamide;
Thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-chloro-benzamide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methyl-benzamide;
Pyridine-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;
(R)—N—[(S)-1-(4-Aminomethyl-benzylcarbamoyl)-2-pyridin-2-yl-ethyl]-3-(4-ethoxy-phenyl)-2-propionylamino-propionamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-isonicotinamide;
Pyridine-2-carboxylic acid [(R)-1-[(S)-1-(4-aminomethyl-3-fluoro-benzylcarbamoyl)-2-phenyl-ethylcarbamoyl]-2-(4-ethoxy-phenyl)-ethyl]-amide;
Thiophene-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;
(R)—N—[(S)-1-(4-Aminomethyl-benzylcarbamoyl)-2-pyridin-3-yl-ethyl]-3-(4-ethoxy-phenyl)-2-propionylamino-propionamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-isonicotinamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-3,3,3-trifluoro-propionamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-chloro-benzamide;
Isoxazole-5-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide;
3-Chloro-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide;
3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-(2-fluoro-phenyl)-ethylcarbamoyl]-2-(4-ethoxy-phenyl)-ethyl]-benzamide;
3-Methyl-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-3-methyl-benzylcarbamoyl)-2-phenyl-ethylcarbamoyl]-2-(4-ethoxy-phenyl)-ethyl]-benzamide;
3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;
3-Chloro-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;
N—[(R)-1-[(S)-1-(4-Aminomethyl-benzylcarbamoyl)-2-thiazol-4-yl-ethylcarbamoyl]-2-(4-ethoxy-phenyl)-ethyl]-4-methyl-benzamide;
3-Methyl-1H-pyrrole-2-carboxylic acid [(R)-1-[(S)-1-(4-aminomethyl-benzylcarbamoyl)-2-benzo thiophen-3-yl-ethylcarbamoyl]-2-(4-ethoxy-phenyl)-ethyl]-amide;
3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;
3-Acetylamino-thiophene-2-carboxylic acid [(R)-1-[(S)-1-(4-aminomethyl-benzylcarbamoyl)-2-benzo thiophen-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-3-methyl-benzamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-2-methyl-benzamide;

3,5-Dimethyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-3-methyl-benzylcarbamoyl)-2-pyridin-3-yl-ethylcarbamoyl]-2-(4-ethoxyphenyl)-ethyl]-benzamide;

3-Acetylamino-thiophene-2-carboxylic acid [(R)-1-[(S)-1-(4-aminomethyl-benzylcarbamoyl)-2-thiophen-3-yl-ethylcarbamoyl]-2-(4-ethoxy-phenyl)-ethyl]-amide;

3-Amino-thiophene-2-carboxylic acid [(R)-1-[(S)-1-(4-aminomethyl-benzylcarbamoyl)-2-benzo thiophen-3-yl-ethylcarbamoyl]-2-(4-ethoxy-phenyl)-ethyl]-amide;

3-Acetylamino-thiophene-2-carboxylic acid [(R)-1-[(S)-1-(4-aminomethyl-benzylcarbamoyl)-2-benzo thiophen-3-yl-ethylcarbamoyl]-2-(4-ethoxy-phenyl)-ethyl]-amide;

3-Chloro-thiophene-2-carboxylic acid [(R)-1-{[(S)-1-(4-aminomethyl-benzylcarbamoyl)-2-phenyl-ethyl]-methyl-carbamoyl}-2-(4-ethoxy-phenyl)-ethyl]-amide;

N—[(R)-1-[(1S,2R)-1-(4-Aminomethyl-benzylcarbamoyl)-2-hydroxy-2-phenyl-ethylcarbamoyl]-2-(4-ethoxy-phenyl)-ethyl]-benzamide;

3-Chloro-thiophene-2-carboxylic acid [(R)-1-[(1S,2R)-1-(4-aminomethyl-benzylcarbamoyl)-2-hydroxy-2-phenyl-ethylcarbamoyl]-2-(4-ethoxy-phenyl)-ethyl]-amide; and N—{(R,S)-1-[(S)-1-(4-Aminomethyl-benzylcarbamoyl)-2-phenyl-ethylcarbamoyl]-2-[4-(2,2,2-trifluoro-ethoxy)-phenyl]-ethyl}-benzamide;

and pharmaceutically acceptable salts and solvates thereof.

In particularly preferred embodiments, the active ingredient is N—[(R)-1-[(S)-1-(4-aminomethyl-benzylcarbamoyl)-2-phenyl-ethylcarbamoyl]-2-(4-ethoxy-phenyl)-ethyl]-benzamide, or a pharmaceutically acceptable salt or solvate thereof. N—[(R)-1-[(S)-1-(4-aminomethyl-benzylcarbamoyl)-2-phenyl-ethylcarbamoyl]-2-(4-ethoxy-phenyl)-ethyl]-benzamide is a plasma kallikrein inhibitor.

The compounds used in certain embodiments of the invention can be prepared according to known procedures, especially those described by Evans et al. ("Benzylamine derivatives as inhibitors of plasma kallikrein" WO2013/005045), using appropriate materials. Moreover, by utilising these procedures, one of ordinary skill in the art can readily prepare additional compounds that can be used in the compositions of the invention.

The compounds used in certain embodiments of the invention may be isolated in the form of their pharmaceutically acceptable salts, such as those described previously herein above.

It may be necessary to protect reactive functional groups (e.g. hydroxy, amino, thio or carboxy) in intermediates used in the preparation of the compounds to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using the methods described in by Evans et al. ("Benzylamine derivatives as inhibitors of plasma kallikrein" WO2013/005045).

Excipients

The compositions of the present invention are adapted for parenteral administration. In particular, the compositions of the present invention may be adapted for intravitreous administration.

The compositions of the invention typically include one or more pharmaceutically acceptable excipients. The term 'excipient' is used herein to describe any ingredient other than the active ingredient which may impart either a functional (e.g. injectability, suspension, stability enhancing, drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form. Potentially suitable excipients include sugars (including but not restricted to glucose, manitol, sorbitol, etc.), salts, carbohydrates and buffering agents.

For example, the composition may optionally include a stabilizing agent or surfactant, such as mannitol, histidine, lysine, glycine, sucrose, fructose, trehalose, lactose, cetrimide, docusate sodium, glyceryl monooleate, sodium lauryl sulfate, or sorbitan esters or a mixture thereof. The stabilising agent or surfactant may optionally be a non-ionic surfactant. Suitable non-ionic surfactants include carboxylic esters, polyethylene glycol esters, glycol esters of fatty acids, ethoxylated aliphatic alcohols, polyoxyethylene surfactants, sorbitol esters, ethoxylated derivatives of sorbitol esters, glycol esters of fatty acids, and poloxamers. Polyoxyethylene surfactants include polyoxyethylenesorbitan fatty acid esters, which are also referred to as polysorbates, e.g. polysorbate 80 (polyoxyethylene sorbitan monooleate, Tween 80), polysorbate 40 and polysorbate 20. Polysorbates, such as polysorbate 80, are commercially available, for example, from Sigma, St. Louis, Mo. In some embodiments, the compositions include a stabilizing agent in an amount of less than about 5% by weight of the compositions, such as less than about 2.5% by weight of the composition. More preferably, the compositions include a stabilizing agent in an amount of less than about 1% by weight of the composition. Yet more preferably and, for example for the purpose of intraocular administration, the compositions include a stabilizing agent in an amount of less than about 0.1% by weight of the composition and even more preferably less 0.05%.

The composition typically includes a buffer. The use of a buffer means that fluctuations in pH can be minimised, which may improve stability. Suitable buffers that can be used in the compositions of the invention include e.g. histidine buffer, acetate buffer, citrate buffer, tartrate buffer, lactate buffer, succinate buffer and phosphate buffer. The pH of the buffer will typically be between about 2 to about 10, e.g. about pH 2, 3, 4, 5, 6, 7, 8, 9 or 10. The pH of the buffer will preferably be about 4 to about 8. Methods of making buffers of the type disclosed herein are well known to the skilled person.

The composition may include ionic or non-ionic tonicity agents, e.g. glycerin, sugars (including glucose, manitol, sorbitol, trehalose, dextrose, lactose etc.), sodium chloride or sodium sulphate. The use of a tonicity agent allows control of the osmolality of the composition. For example, it may be desirable that a composition for intravitreal injection is isotonic to the vitreous so as to not disrupt the fluid balance of the vitreous and surrounding tissues. Typically, the compositions of the invention comprise a tonicity agent in an amount from about 0.1% to about 30% by weight of the compositions, e.g. about 0.1%, 0.2%, 0.3%, 0.4%, 0.5%, 0.6%, 0.7%, 0.8%, 0.9%, 1%, 2.5%, 5%, 10%, 15%, 20%, 25% or 30% by weight of the composition. The compositions of the invention may be hypotonic, isotonic or hypertonic and typically have an osmolality of from about 250 to about 350 mOsmol/kg. For example, the compositions may have an osmolality of 250, 260, 270, 280, 290, 300, 310, 320, 330, 340 or 350 mOsmol/kg. The skilled person will understand that the amount of tonicity agent used may vary depending on the particular choice of agent and on the other components in the composition.

The composition may include an antioxidant, such as acetone, sodium bisulfite, butylated hydroxy anisole, butylated hydroxy toluene, cysteine, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium or ascorbic acid. Alternatively, in particular for intraocular use of the composition, packaging may be configured in a manner that controls the potential for oxidation of the composition, including for example purging with an inert gas during manufacture.

Additional Therapeutic Agents

The compositions of the invention may include one or more other therapeutic agents. For example, the compositions may include one or more of an agent that inhibits platelet-derived growth factor (PDGF), an agent that inhibits endothelial growth factor (VEGF), and an agent that inhibits integrins, for example integrin alpha5beta1. The compositions may also include one or more steroids. The compositions may also involve other agents including serine proteases, such as ocriplasmin. The compositions may also include other agents that inhibit plasma kallikrein and/or other inhibitors of inflammation. The composition may also include antagonists of bradykinin, for example antagonists of the bradykinin B2 receptor such as the drug icatibant.

Specific examples of therapeutic agents that may be included in the compositions of the invention include those disclosed in EP2281885A and by S. Patel in Retina, 2009 June; 29(6 Suppl):S45-8.

In some embodiments, the plasma kallikrein inhibitor of formula I and the one or more other therapeutic agents may exist in the same aqueous suspension pharmaceutical composition. In other embodiments, the plasma kallikrein inhibitor of formula I and the one or more other therapeutic agents may exist in different pharmaceutical compositions (one of which is an aqueous suspension pharmaceutical composition). The compositions may be administered separately, sequentially or simultaneously.

Administration, Medical Treatments and Uses

The invention also provides a method for treating a disease or condition mediated by plasma kallikrein comprising parenteral administration of a pharmaceutical composition of the invention to a mammal.

The invention also provides a pharmaceutical composition of the invention for use in treating a disease or condition mediated by a plasma kallikrein inhibitor of formula I.

The invention also provides the use of a plasma kallikrein inhibitor of formula I in the manufacture of a medicament for treating a disease or condition mediated by a serine protease.

The uses and methods are useful for the treatment of a disease or condition mediated by plasma kallikrein. For example, the uses and methods are useful for the treatment of impaired visual acuity, diabetic retinopathy, macular oedema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post-operative surgery. Preferably, the uses and methods are useful for the treatment of retinal vascular permeability associated with diabetic retinopathy or diabetic macular oedema. In some embodiments, the uses and methods are useful for the treatment of microvascular complications of a disease state.

The compositions of the invention are suitable for parenteral administration. Accordingly, the compounds of the invention may be administered directly e.g. into the blood stream, into subcutaneous tissue, into muscle, or into an internal organ.

Suitable means for parenteral administration include intraarterial, intraperitoneal, intrathecal, intraventricular, intraurethral, intrasternal, intracranial, intramuscular, intrasynovial, subcutaneous, intravenous or intravitreous. In some embodiments, the compositions may be administered via surgical incision into the subcutaneous tissue, muscular tissue or directly into specific organs.

In one preferred embodiment, the composition is administered intravitreously. To improve patient compliance when administering the compositions intravitreously, it is preferred to administer the composition relatively infrequently. For example, the composition may be administered once per week, once every two weeks, once per month, once every three months or once every six months. Preferably, the composition will be administered once per month, once every three months or once every six months. Relatively infrequent administration, and hence improved patient compliance, is achieved with the compositions of the present invention because of the long-action that results from suspensions of poorly soluble compounds. It is known in the art that dissolution times of compounds are generally extended when a compound is in crystalline form, compared to amorphous solids, because of the increased lattice energy. Where intravitreous administration is envisaged, the composition may include crystalline or amorphous protease inhibitor or a mixture of both crystalline and amorphous protease inhibitor and may preferably include crystalline protease inhibitor.

In another preferred embodiment, the composition is administered intravenously. This mode of administration may be particularly preferred where an almost-immediate effect on the patient is required, such as for the treatment of emergencies and/or life threatening conditions. The suspension compositions of the invention have been found to substantially mitigate the problems in the art associated with intravenous administration of poorly soluble drugs, such as precipitation in vivo. The use of nanosuspension compositions is particularly preferred for intravenous administration, because such compositions typically require only a small amount of stabilizing agent to prevent particle agglomeration in vivo. In particular, for intravenous administration, it is preferred to use a composition including particles of active ingredient having an average (D50) size of from about 10 nm to about 1000 nm, such as from about 10 nm to about 500 nm. Where intravenous administration is envisaged, the composition may include crystalline or amorphous protease inhibitor or a mixture of both crystalline and amorphous protease inhibitor and may preferably include amorphous protease inhibitor. Suitable devices for parenteral administration include needle (including microneedle) injectors, needle-free injectors and infusion techniques.

In some embodiments, the uses and methods involve combination therapy. For example, the uses and methods may further comprise laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema" Ophthalmology. 27 Apr. 2010).

It is envisaged that the compositions of the invention will take the form of sterile aqueous suspensions. The preparation of parenteral formulations under sterile conditions, for example, by lyophilisation and reconstitution, may readily be accomplished using standard pharmaceutical techniques well known to those skilled in the art. For example, a suitable method for sterilising the compositions of the present invention may be terminal sterilisation. The terminal sterilisation method is described in US Pharmacopeia USP<1211> Sterilization and Sterility Assurance of Compendial Articles and USP<1222> Terminally Sterilized Pharmaceutical Products-Parametric Release.

The compositions may be administered to the patient under the supervision of an attending physician.

Processes

The present invention further relates to processes for preparing pharmaceutical compositions of the invention. In some preferred embodiments, the process includes the use of polysorbate 80 or polysorbate 20 as a stabilising agent and dextrose or trehalose as a tonicity agent. More preferably, the process includes the use of polysorbate 20 as a stabilising agent and trehalose as a tonicity agent.

The process optionally includes reducing the particle size of the active ingredient. In some embodiments, the particle size of the active ingredient may be reduced when the active ingredient is suspended in the aqueous vehicle of the composition. In this embodiment, suitable methods of reducing the particle size of the active ingredient include precipitation processes, processes using wet ball milling such as bead milling or pearl milling, or processes using high pressure homogenisation. Alternatively, the particle size of the active ingredient may be reduced using high shear fluid processing (for example by use of Microfluidics high shear fluid processor). In other embodiments, the method of reducing the particle size of the active ingredient may occur in the dry form prior to its suspension in the aqueous vehicle of the composition. Examples of methods of reducing the particle size of an active ingredient in dry form include ball milling, jet milling and roller milling. Such methodologies are known in the art, see "Pharmaceutical Preformulation and Formulation" Ed. Mark Gibson, Informa Healthcare, New York, 2009, Chapter 6 "Preformulation as an Aid to Product Design in Early Drug Development", "Pharmaceutical nanocrystals" Wang G. D. et al Current Opinion in Chemical Engineering Volume 1 issue 2 pages 102-107 and "Drug nanocrystals for the formulation of poorly soluble drugs and its application as a potential drug delivery system" Gao L. et al J Nanopart Res 2008; 10:845-862. Microfluidization processors are available from Microfluidics, 90 Glacier Drive Suite 1000, Westwood, Mass. 02090 USA.

Definitions

The term "practically insoluble or insoluble" means an aqueous solubility of <0.1 mg/mL.

The term "very slightly soluble" means an aqueous solubility of 0.1-1 mg/mL.

The term "slightly soluble" means an aqueous solubility of 1-10 mg/mL.

The term "sparingly soluble" means an aqueous solubility of 10-33 mg/mL.

References to "particles" of the composition are references to particles of the active ingredient.

The term "D50" means the median value of the particle size distribution. (according to International Standards Organization method ISO 13320).

The term "aqueous" means that the composition includes water as a solvent. Typically, the content of free water in the composition is greater than or equal to about 35% by weight, preferably more than about 50% by weight of the composition, e.g. more than about 60%, 65%, 70%, 75%, 80%, 85%, 90%, 95%, 97%, 98% or 99% by weight of the composition.

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

The term "alkyl" includes saturated hydrocarbon residues including:
  linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.
  branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.
  each optionally substituted as stated above.

The term "alkoxy" includes O-linked hydrocarbon residues including:
  linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.
  branched groups of between 3 and 6 carbon atoms ($C_3$-$C_6$) or of between 3 and 4 carbon atoms ($C_3$-$C_4$).

Examples of such alkoxy groups include, but are not limited to, $C_3$-iso-propoxy, and $C_4$-sec-butoxy and tert-butoxy.

each optionally substituted as stated above.

Unless otherwise stated, halo is selected from Cl, F, Br and I.

Cycloalkyl is as defined above. Cycloalkyl groups may contain from 3 to 10 carbon atoms, or from 4 to 10 carbon atoms, or from 5 to 10 carbon atoms, or from 4 to 6 carbon atoms. Examples of suitable monocyclic cycloalkyl groups include cyclopropyl, cyclobutyl, cyclopentyl, cyclohexyl and cycloheptyl. Examples of suitable bicyclic cycloalkyl groups include decahydronaphthalene and octahydro-1H-indene Examples of suitable cycloalkyl groups, when fused with aryl, include indanyl and 1,2,3,4-tetrahydronaphthyl.

Heterocycloalkyl is as defined above. Examples of suitable heterocycloalkyl groups include oxiranyl, aziridinyl, azetidinyl, tetrahydrofuranyl, pyrrolidinyl, tetrahydropyranyl, piperidinyl, N-methylpiperidinyl, morpholinyl, N-methyl morpholinyl, piperazinyl, N-methylpiperazinyl, azepanyl, oxazepanyl and diazepanyl.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above).

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above).

The term "C-linked", such as in "C-linked heterocycloalkyl", means that the heterocycloalkyl group is joined to the remainder of the molecule via a ring carbon atom.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —COalkyl and —$(CH_2)_b COOR^{10}$, "—" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming prodrugs are described in 'The Practice of Medicinal Chemistry, $2^{nd}$ Ed. pp 561-585 (2003) and in F. J. Leinweber, Drug Metab. Res., 1987, 18, 379.

The compounds of formula (I) as described herein can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds used in the compositions of the invention exist in one or more geometrical, optical, enantiomeric, diastereomeric and tautomeric forms, including but not limited to cis- and trans-forms, E- and Z-forms, R-, S- and meso-forms, keto-, and enol-forms, then, unless otherwise stated, a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

In the context of the present invention, references herein to "treatment" include references to curative, palliative and prophylactic treatment.

MODES FOR CARRYING OUT THE INVENTION

The invention is further illustrated by the followings examples. It will be appreciated that the examples are for illustrative purposes only and are not intended to limit the invention as described above. Modification of detail may be made without departing from the scope of the invention.

Example A—Synthetic Examples

Compounds of formula I may be prepared according to the methods described in Evans et al. ("Benzylamine derivatives as inhibitors of plasma kallikrein" WO2013/005045).

Example B1—Preparation Via Wet Ball Milling and Analysis of Aqueous Suspension Pharmaceutical Composition of Milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride All product materials were weighed and dispensed in a laminar flow hood. A stock solution of hydrochloric acid was prepared by adding concentrated hydrochloric acid (10.0 mL) to sterile water and making up to 100.0 mL. A stock solution of polysorbate 20 was prepared by adding polysorbate 20 (10.0 g) to sterile water and making up to 100.0 mL. The milling vehicle was prepared by dissolving histidine (10.10 g), hydrochloric acid (26.7 mL of the prepared stock solution), polysorbate 20 (6.50 mL of the prepared stock solution) and trehalose (565.94 g) in sterile water bringing the solution to 6500 mL with sterile water. The solution was sterile filtered.

The milling vehicle (500 mL) was added to a 2000 mL milling vessel and N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (26.57 g) was suspended in it. Milling media (0.5 mm YTZ ceramic media) was added until its level was slightly below that of the suspension (approximately 1000 mL). The container was capped and sealed before milling.

The milling vessel was rolled at a rotational speed sufficient to ensure that the level of the cascading media was at about a 45° angle to the horizontal (approximately 111 rpm). The suspension was processed until the mean particle size met the required target of 0.1 microns (approximately 36 hours, FIG. 1). The milling containers were sanitized with isopropanol and placed in a laminar-flow hood prior to being sampled.

After the target particle-size distribution was achieved, the suspension/media slurry was transferred to a filtration funnel (Chemglass 1 L funnel with 40-60 micron frit). Sterile-filtered nitrogen was used to pressurize the funnel. The suspension was filtered into a sterile bulk container to afford an aqueous suspension pharmaceutical composition of milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (440 mL, nominally 50 mg/mL with respect to N—[(R)-1-[(S)-1-(4-aminomethyl-benzylcarbamoyl)-2-phenyl-ethylcarbamoyl]-2-(4-ethoxy-phenyl)-ethyl]-benzamide free base). The finished suspension was characterized by testing for appearance, assay, particle-size distribution, pH, and osmolality.

Appearance: slightly white, slightly pink suspension, settled material easily re-dispersed Assay by HPLC: 91.1% label claim
(label claim=50 mg/mL with respect to N—[(R)-1-[(S)-1-(4-aminomethyl-benzylcarbamoyl)-2-phenyl-ethylcarbamoyl]-2-(4-ethoxy-phenyl)-ethyl]-benzamide free base)

pH: 5.2

Particle size distribution: $D_{50}$=0.07 μm

Osmolality: 297 mOsm/kg

The HPLC assay referred to above was carried out using the following reagents, apparatus and instrumentation:

Reagents
1) Acetonitrile, HPLC grade (Fisher Part No. A998 or equivalent) (Diluent preparations)
2) Acetonitrile: 99.9%, for HPLC, far UV-cutoff (Acros Organics Part No. AC26826-0025 or equivalent) (Mobile Phase)
3) Deionized Water (Fisher Part No. W-5 or equivalent)
4) Trifluoroacetic Acid (TFA): Optima grade for LC/MS, 1-mL ampoule (Fisher Part No. A11610X1AMP or equivalent)
5) N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride reference standard Apparatus
1) 100-mL Class A low-actinic volumetric flasks with stopper
2) Class A pipettes
3) Sample filtration equipment
disposable syringes with Luer-Lok Tip (5 or 10-mL)
0.22 mm PTFE filters-25 mm
4) Weighing paper and spatulas
5) 5-place analytical balance
6) Vortex
7) 1-L Class A volumetric flask with ground glass stopper
8) Low-actinic/amber HPLC vials with PTFE septa (Waters 600000669CV)

Instrumentation
Waters Alliance HPLC or Agilent 1100 HPLC or equivalent, capable of delivering flow rates of 1.0 mL/min and equipped with a UV Detector or Photodiode Array Detector capable of monitoring at 220 nm.

The HPLC assay referred to above was carried out using the following procedure and analysis:

Diluent Preparation
Prepare a diluent solution of 50% acetonitrile/50% water, mix well and equilibrate to room temperature prior to use.

Mobile Phase Preparation (Per 1 L of Mobile Phase Required)
1) Mobile Phase A—0.1% TFA in water:
  a) Add 1 mL of trifluoroacetic acid to approximately 950 mL of water.
  b) Mix thoroughly
  c) Bring to 1 L volume with water.
2) Mobile Phase B—0.1% TFA in far UV-cutoff acetonitrile:
  d) Add 1 mL of trifluoroacetic acid to approximately 950 mL of acetonitrile.
  e) Mix thoroughly
  f) Bring to 1 L volume with acetonitrile.

Sample Preparation
1) Mix the suspension in a sealed vial (container) by vortex for approximately 30 seconds
2) Note appearance and observations of settling
3) Weigh 1.0 g (±0.1 g) of the suspension into a 100 mL volumetric flask.
4) Bring to volume with sufficient diluent
5) Cap flask and mix thoroughly by inversion Preparation of Reference Standards (Using Class a Glassware)
N—[(R)-1-[(S)-1-(4-aminomethyl-benzylcarbamoyl)-2-phenyl-ethylcarbamoyl]-2-(4-ethoxy-phenyl)-ethyl]-benzamide Stock Standard [approximately 500 mg/mL]
1) Using a 5-place analytical balance, accurately weigh about 25.0 mg of N—[(R)-1-[(S)-1-(4-aminomethyl-benzylcarbamoyl)-2-phenyl-ethylcarbamoyl]-2-(4-ethoxy-phenyl)-ethyl]-benzamide reference standard into a 50-mL low-actinic volumetric flask. Record the weight.
2) Bring to volume with diluent, cap and mix well.
3) Allow to equilibrate to room temperature.
4) The actual N—[(R)-1-[(S)-1-(4-aminomethyl-benzylcarbamoyl)-2-phenyl-ethylcarbamoyl]-2-(4-ethoxy-phenyl)-ethyl]-benzamide (free base) concentration is calculated from the recorded weight and the certified purity of the reference standard.

Chromatographic Conditions
1) Analytical Column:
  a) Packing: Mac-Mod Analytical ACE-3 C18
  b) Size: 4.6×150 mm, 3 μm particle size
2) Mobile phase gradient:

| Time (Min) | % A | % B |
|---|---|---|
| 0 | 80 | 20 |
| 15 | 35 | 65 |
| 20 | 35 | 65 |
| 25 | 20 | 80 |
| 30 | 20 | 80 |
| 30.1 | 80 | 20 |
| 35 | 80 | 20 |

2) Flow Rate: 1.0 mL/Min
3) Detector: 220 nm
4) Column Temperature: 35° C.
5) Injection Volume: 10 mL 6) Run Time: 35 minutes
7) Mobile Phase A: 0.1% TFA in water
8) Mobile Phase B: 0.1% TFA in far UV-cutoff acetonitrile
9) Purge Solvent: 50/50, water/acetonitrile (if required by instrument)
10) Needle Wash: 100% acetonitrile (if required by instrument)

HPLC Data Analysis

1) Chromatograms are extracted at 220 nm
2) Peaks of interest are quantified against the response factor of the working standard
3) The concentration of the peak of interest is then calculated
4) The label claim of the sample is calculated Particle Size Distribution Particle-size measurements were made with a Horiba LA-950 V2 laser-diffraction particle-size analyzer using 1% polysorbate 20 in 0.9% sodium chloride solution and a refractive index 1.611 (i=0.2). The results after 36 hours of milling are shown in FIG. 1. Median particle size=0.08157 (μm); D10=0.05935 (μm); D90=0.12416 (μm).

Osmolality

Osmolality was measured using the Advanced Micro-Osmometer Model 3320, available from Advanced Instruments Inc, by the method of freezing point depression.

Example B2—Stability of Aqueous Suspension Pharmaceutical Composition of Milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride Aqueous suspension pharmaceutical composition of milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (440 mL, nominally 50 mg/mL with respect to N—[(R)-1-[(S)-1-(4-aminomethyl-benzyl-carbamoyl)-2-phenyl-ethylcarbamoyl]-2-(4-ethoxy-phenyl)-ethyl]-benzamide free base) was prepared as described in Example B1. Samples of the suspension were packed in volumes of 1 mL inside 2 mL Type 1 glass vials with PTFE lined screw cap closures and stored at two stability conditions of 5° C. and 25° C./60% relative humidity (rh). Samples were tested for appearance, assay, particle-size distribution, pH, and osmolality at the start of the study and at time-points of five weeks and three months. Results are shown in Table i.

TABLE i

|  | Initial | Five weeks 5° C. | Three months 5° C. | Five weeks 25° C./ 60% rh | Three months 25° C./ 60% rh |
| --- | --- | --- | --- | --- | --- |
| Appearance | slightly white, slightly pink suspension, settled material easily re-dispersed | as initial | as initial | as initial | as initial |
| Assay (% Label Claim) | 91.1 | 92.0 | 93.0 | 91.1 | 92.1 |

TABLE i-continued

|  | Initial | Five weeks 5° C. | Three months 5° C. | Five weeks 25° C./ 60% rh | Three months 25° C./ 60% rh |
| --- | --- | --- | --- | --- | --- |
| Particle-size distribution (D50, μm) | 0.07 | 0.09 | 0.07 | 0.09 | 0.08 |
| pH | 5.2 | 5.1 | 5.2 | 4.9 | 4.7 |
| Osmolality (mOsm/kg) | 297 | 292 | 296 | 291 | 297 |

Example C—Preparation Via High Shear Fluid Processing and Analysis of Aqueous Suspension Pharmaceutical Composition of Milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride All product materials were weighed and dispensed in a laminar flow hood. A stock solution of hydrochloric acid was prepared by adding concentrated hydrochloric acid (10.0 mL) to sterile water and making up to 100.0 mL. A stock solution of polysorbate 20 was prepared by adding polysorbate 20 (10.0 g) to sterile water and making up to 100.0 mL. The milling vehicle was prepared by dissolving histidine (10.10 g), hydrochloric acid (26.7 mL of the prepared stock solution), polysorbate 20 (6.50 mL of the prepared stock solution) and trehalose (565.94 g) in sterile water bringing the solution to 6500 mL with sterile water. The solution was sterile filtered.

N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (7.5 g) was suspended in the milling vehicle (75 g) and optionally premixed using a roto-stator homogenizer. The resulting suspension was processed on an M-110P processor (Microfluidics, 90 Glacier Drive, Suite 1000, Westwood, Mass. 02090, USA) through the H30Z (200 μm)-G10Z (87 μm) IXC configuration at 30,000 psi. An ice water bath was placed around the cooling coil to remove the heat generated during processing. The processing was repeated through several passes (processing cycles). The D90 particle size met the required target of 0.23 microns after approximately 10 passes.

The processed suspension was characterized by testing for particle size distribution and Transmission Electron Microscopy (TEM).

Particle Size Distribution

Figure 2:
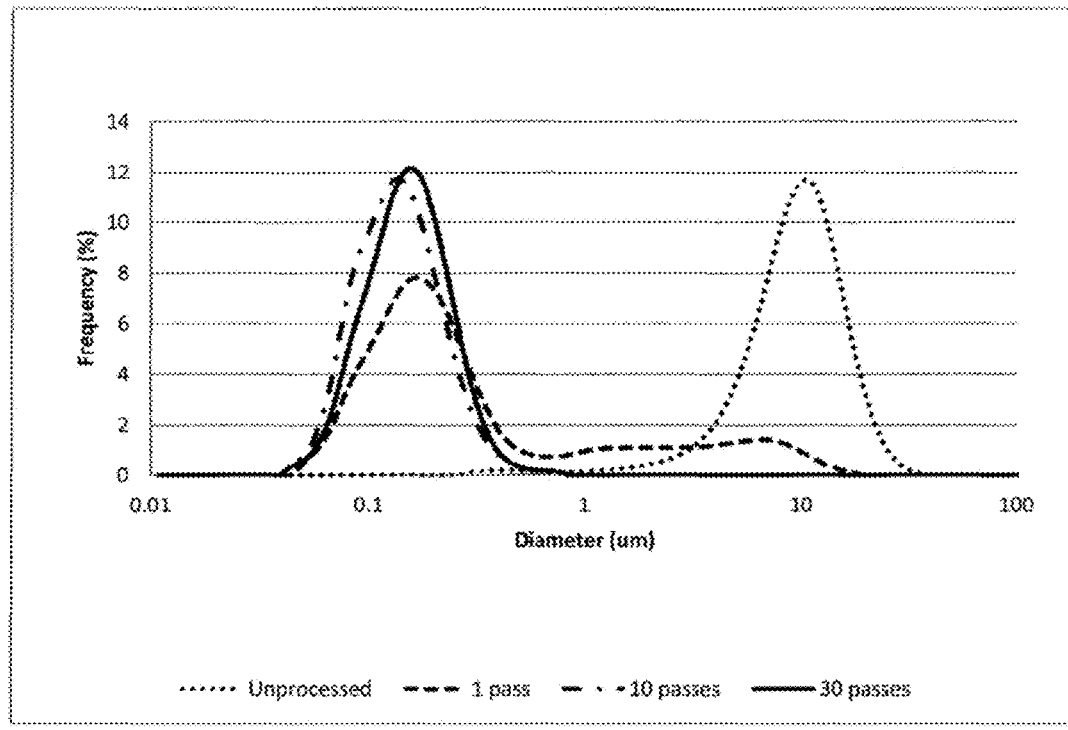
FIG. 2 shows the particle-size distribution obtained from laser-diffraction analysis of the suspension of Example C.

Particle-size measurements were made with a Horiba LA-950 laser-diffraction particle-size analyzer using 0.1% polysorbate 80 in 0.9% sodium chloride solution. The results are shown in Table ii and FIG. 2.

TABLE ii

| Number of processing cycles | D10 (μm) | D50 (μm) | D90 (μm) |
| --- | --- | --- | --- |
| Unprocessed | 4.171 | 9.047 | 15.774 |
| 1 | 0.086 | 0.193 | 4.033 |
| 5 | 0.074 | 0.138 | 0.297 |
| 10 | 0.072 | 0.127 | 0.230 |
| 20 | 0.073 | 0.128 | 0.234 |
| 30 | 0.079 | 0.142 | 0.249 |

Transmission Electron Microscopy (TEM)

Figure 3:
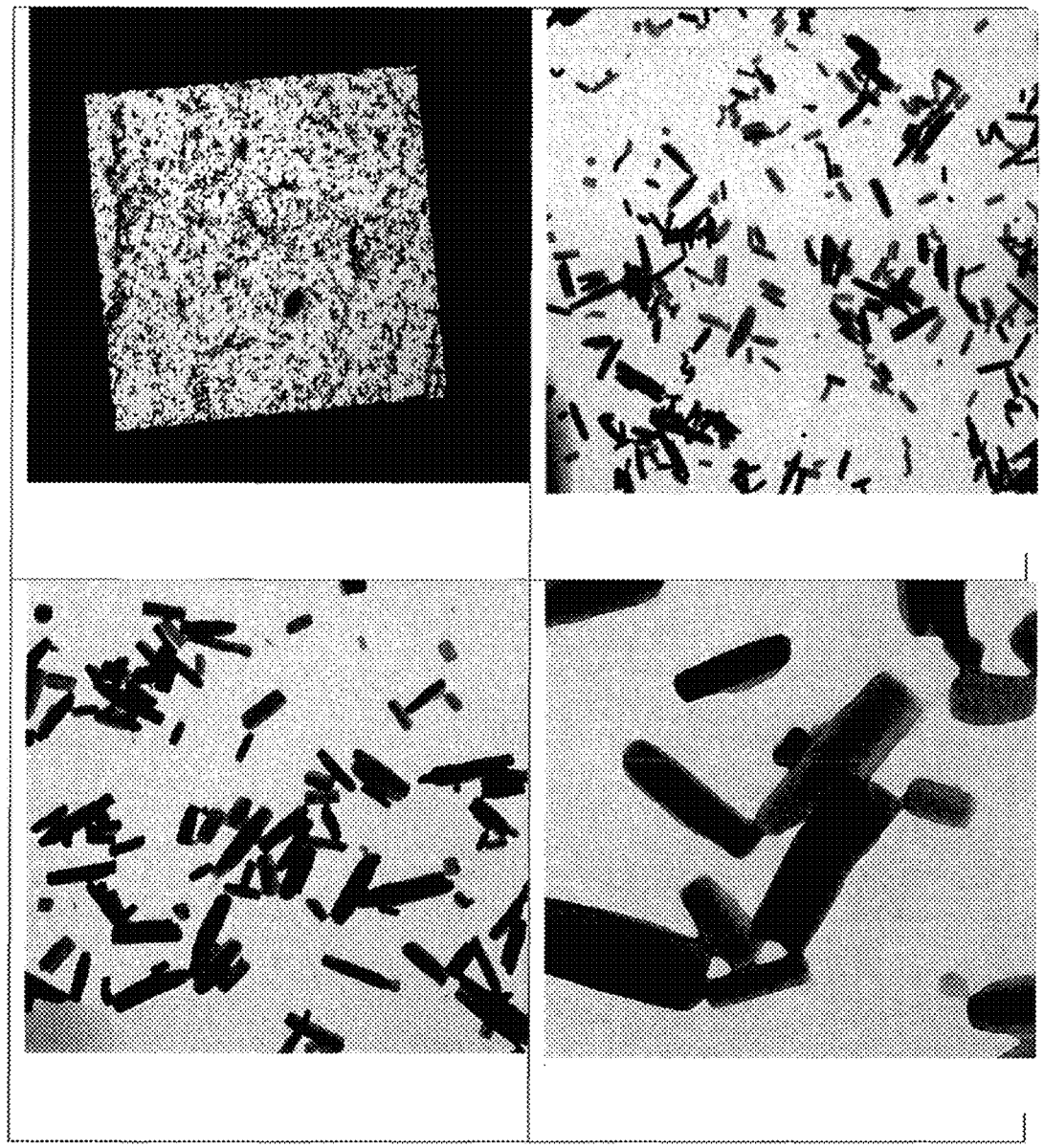
FIG. 3 shows images obtained from transmission electron microscopy (TEM) analysis of the suspension of Example C.

A drop of the processed suspension (20 passes) was placed onto a coated TEM grid and a drop of 1% aqueous uranyl acetate was used to add contrast. This preparation was dried using a filter paper technique, mounted into the TEM (Philips CB120 BioTwin, Eindhoven, Holland) and analysed at 120 kV under ultra-high vacuum conditions. Representative images are shown in FIG. 3.

Example D—Preparation Via High Shear Fluid Processing and Analysis of Aqueous Suspension of Milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (5 g) was suspended in de-ionised water (100 g) and optionally premixed using a roto-stator homogenizer. The resulting suspension was processed on an M-110P processor (Microfluidics, 90 Glacier Drive, Suite 1000, Westwood, Mass. 02090, USA) through the H30Z (200 μm)-G10Z (87 μm) IXC configuration at 30,000 psi. An ice water bath was placed around the cooling coil to remove the heat generated during processing. The processing was repeated through several passes (processing cycles). The D90 particle size met the required target of 0.24 microns after approximately 10 passes.

The processed suspension was characterized by testing for particle size distribution and Transmission Electron Microscopy (TEM).

Particle Size Distribution

Figure 4:
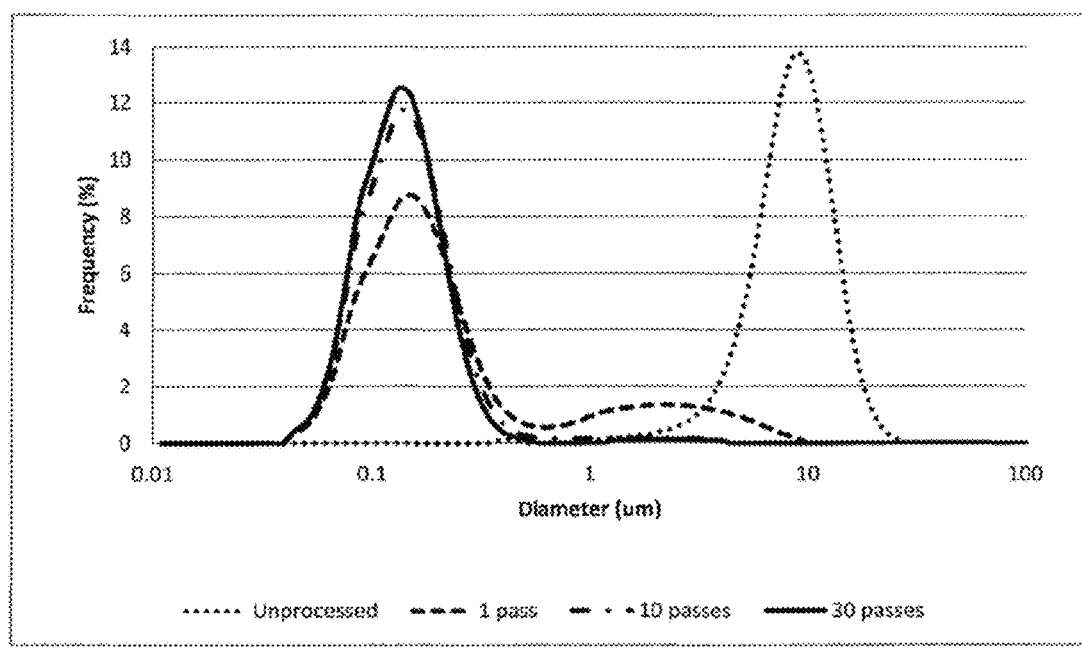
FIG. 4 shows the particle-size distribution obtained from laser-diffraction analysis of the suspension of Example D.

Particle-size measurements were made with a Horiba LA-950 laser-diffraction particle-size analyzer using 0.1% polysorbate 80 in 0.9% sodium chloride solution. The results are shown in Table iii and FIG. 4.

TABLE iii

| Number of processing cycles | D10 (μm) | D50 (μm) | D90 (μm) |
|---|---|---|---|
| Unprocessed | 4.456 | 8.070 | 12.992 |
| 1 | 0.078 | 0.161 | 1.976 |
| 5 | 0.076 | 0.143 | 0.276 |
| 10 | 0.074 | 0.131 | 0.244 |
| 20 | 0.074 | 0.131 | 0.248 |
| 30 | 0.073 | 0.125 | 0.218 |

Transmission Electron Microscopy (TEM)

Figure 5:
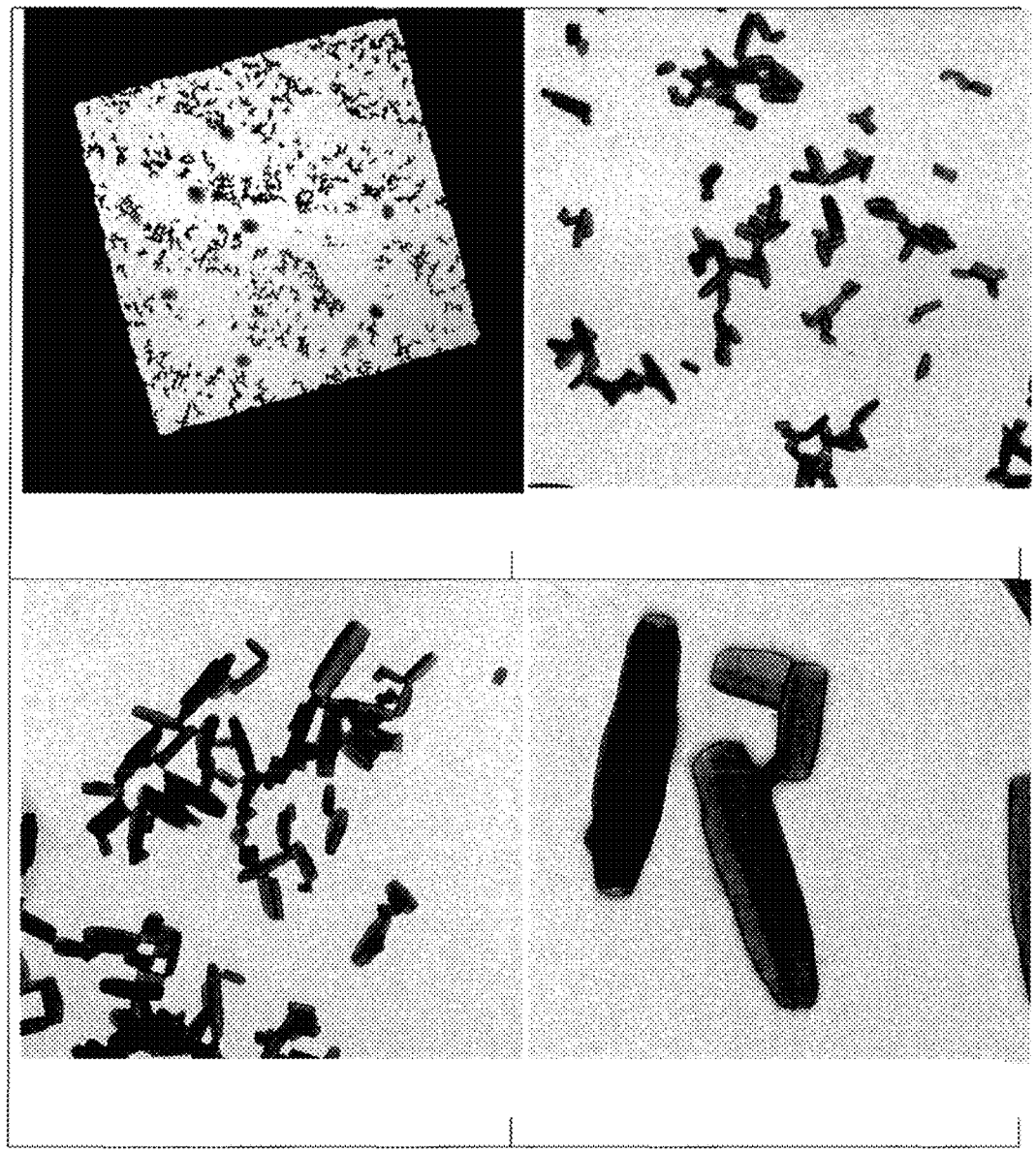
FIG. 5 shows images obtained from transmission electron microscopy (TEM) analysis of the suspension of Example D.

A drop of the processed suspension (20 passes) was placed onto a coated TEM grid and a drop of 1% aqueous uranyl acetate was used to add contrast. This preparation was dried using a filter paper technique, mounted into the TEM (Philips CB120 BioTwin, Eindhoven, Holland) and analysed at 120 kV under ultra-high vacuum conditions. Representative images are shown in FIG. 5.

Example E—Ocular Tissue Concentration Study of N—[(R)-1-[(S)-1-(4-aminomethyl-benzylcarbamoyl)-2-phenyl-ethylcarbamoyl]-2-(4-ethoxy-phenyl)-ethyl]-benzamide at Twelve Weeks Following a Single Intravitreal Dose Administration in Pigmented Rabbits An aqueous suspension pharmaceutical composition of milled N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride was prepared according to Example B1. The resulting nominal 50 mg/mL suspension was diluted with the milling vehicle (prepared according to Example B1) into dosing formulations for intravitreal injection. Five experimentally nave male and female Dutch-belted rabbits, approximately 5 months old and weighing 1.6 to 2.2 kilograms at the outset of the study were assigned to treatment groups as shown in Table iv.

TABLE iv

| Group | Dose Level* (μg/eye) | Dose Volume (mL/eye) | Dosing Concentration* (μg/mL) | Number of Animals Male | Female |
|---|---|---|---|---|---|
| 1. Suspension Low-Dose | 15 | 0.05 | 300 | 2 | 1 |
| 2. Suspension High-dose | 150 | 0.05 | 3000 | 1 | 2 |

*Concentrations and dose levels were expressed as N-[(R)-1-(S)-1-(4-aminomethyl-benzylcarbamoyl)-2-phenyl-ethylcarbamoyl]-2-(4-ethoxy-phenyl)-ethyl]-benzamide free base form (the active ingredient)

Animals were administered bilateral intravitreal doses of the suspension formulations once on Day 1. On Day 86, the vitreous humors and retina (with choroid) tissues were analysed for active ingredient concentration.

Vitreous humor concentrations of active ingredient were significant on Day 86 for the high-dose group. Active ingredient vitreous humor concentrations for the low-dose group animals on Day 86 ranged from 0.216 to 935 ng/mL. The average active ingredient vitreous humor concentration for the high-dose rabbits was 27,800 ng/mL and concentrations ranged from 2500 to 56,500 ng/mL. In the low-dose and high-dose groups, the average active ingredient retina (with choroid) tissue concentrations were 1620 ng/g and 44,500 ng/g, respectively. The vitreous concentrations demonstrate the slow elimination of the active ingredient when delivered as an aqueous suspension pharmaceutical composition and the retina (with choroid) levels confirm that the active ingredient was able to reach the posterior ocular tissues.

It will be understood that the invention has been described by way of example only and modifications may be made whilst remaining within the scope and spirit of the invention.

What is claimed is:

1. A process for preparing an aqueous pharmaceutical suspension composition suitable for parenteral administration in a mammalian patient, the aqueous pharmaceutical suspension comprising a compound of formula I having an aqueous solubility of less than 1 mg/mL:

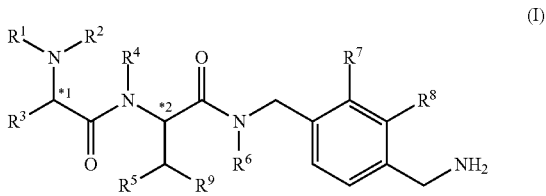

wherein:
$R^1$ is H, alkyl, —COalkyl, —COaryl, —COheteroaryl, —CO$_2$alkyl, —(CH$_2$)$_a$OH, —(CH$_2$)$_b$COOR$^{10}$, —(CH$_2$)$_c$CONH$_2$, —SO$_2$alkyl, or —SO$_2$aryl;
$R^2$ is H or alkyl;
$R^3$ is H, alkyl, —(CH$_2$)$_d$aryl, —(CH$_2$)$_e$heteroaryl, —(CH$_2$)$_f$cycloalkyl, —(CH$_2$)$_g$heterocycloalkyl, —CH(cycloalkyl)$_2$, or —CH(heterocycloalkyl)$_2$;
$R^4$ and $R^6$ are independently H or alkyl;
$R^5$ is H, alkyl, alkoxy, or OH;

or R⁴ and R⁵, together with the atoms to which they are attached, form a 5- or 6-membered azacycloalkyl structure;

R⁷ and R⁸ are independently H, alkyl, alkoxy, CN, or halo;
R⁹ is aryl or heteroaryl;
R¹⁰ is H or alkyl;
a, b, c, d, e, f and g are, independently, 1, 2 or 3;
*1 and *2 denote chiral centres;
alkyl is a linear saturated hydrocarbon having up to 10 carbon atoms ($C_1$-$C_{10}$) or a branched saturated hydrocarbon of between 3 and 10 carbon atoms ($C_3$-$C_{10}$); wherein the alkyl is optionally substituted with 1 or 2 substituents that are, independently, ($C_3$-$C_{10}$)cycloalkyl, ($C_1$-$C_6$)alkoxy, OH, CN, $CF_3$, $COOR^{11}$, fluoro, or $NR^{11}R^{12}$;
cycloalkyl is a mono- or bi-cyclic saturated hydrocarbon of between 3 and 10 carbon atoms; wherein the cycloalkyl is optionally fused to an aryl group;
heterocycloalkyl is a C-linked or N-linked 3 to 10 membered saturated, mono- or bi-cyclic ring, wherein said heterocycloalkyl ring comprises 1, 2 or 3 heteroatoms that are, independently, N, $NR^{11}$, or O;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); wherein the alkoxy is optionally substituted with 1 or 2 substituents that are, independently, ($C_3$-$C_{10}$)cycloalkyl, OH, CN, $CF_3$, $COOR^{11}$, fluoro, or $NR^{11}R^{12}$;
aryl is phenyl, biphenyl or naphthyl; wherein the aryl is optionally substituted with up to 5 substituents that are, independently, alkyl, alkoxy, OH, halo, CN, $COOR^{11}$, $CF_3$, or $NR^{11}R^{12}$;
heteroaryl is a 5, 6, 9 or 10 membered mono- or bi-cyclic aromatic ring containing 1, 2 or 3 ring members that are, independently, N, $NR^{11}$, S and O; wherein the heteroaryl is optionally substituted with 1, 2 or 3 substituents that are, independently, alkyl, alkoxy, OH, halo, CN, $COOR^{11}$, $CF_3$, or $NR^{11}R^{12}$;
$R^{11}$ and $R^{12}$ are H or alkyl;
or a tautomer, stereoisomer, pharmaceutically acceptable salt, or solvate thereof;
the process comprising suspending particles of the active ingredient that is a compound of formula I, or a pharmaceutically acceptable salt thereof, in an aqueous vehicle.

2. The process of claim 1, further comprising reducing the particle size of the active ingredient.

3. The process of claim 2, wherein the particle size of the active ingredient is reduced in the aqueous vehicle.

4. The process of claim 3, wherein the particle size is reduced using precipitation, wet ball milling, or high pressure homogenisation.

5. The process of claim 3, wherein the particle size is reduced using high shear fluid processing.

6. The process of claim 2, wherein the particle size of the active ingredient is reduced in the dry form prior to suspension in the aqueous vehicle.

7. The process of claim 6, wherein the particle size is reduced using ball milling, jet milling, or roller milling.

8. The process of claim 1, wherein the active ingredient is:
(S)—N-(4-Aminomethyl-benzyl)-2-[(R)-3-(4-ethoxy-phenyl)-2-propionylamino-propionylamino]-3-phenyl-propionamide;
N—[(R)-1-[(S)-1-(4-Aminomethyl-benzylcarbamoyl)-2-phenyl-ethylcarbamoyl]-2-(4-ethoxy-phenyl)-ethyl]-benzamide;
{(R)-1-[(S)-1-(4-Aminomethyl-benzylcarbamoyl)-2-phenyl-ethylcarbamoyl]-2-cyclohexyl-ethylamino}-acetic acid;
(S)—N-(4-Aminomethyl-3-fluoro-benzyl)-2-[(R)-3-(4-ethoxy-phenyl)-2-propionylamino-propionylamino]-3-phenyl-propionamide;
(S)—N-(4-Aminomethyl-2-chloro-benzyl)-2-[(R)-3-(4-ethoxy-phenyl)-2-propionylamino-propionylamino]-3-phenyl-propionamide;
(S)—N-(4-Aminomethyl-benzyl)-3-(3,4-dichloro-phenyl)-2-[(R)-3-(4-ethoxy-phenyl)-2-propionylamino-propionylamino]-propionamide;
(S)—N-(4-Aminomethyl-3-chloro-benzyl)-2-[(R)-3-(4-ethoxy-phenyl)-2-propionylamino-propionylamino]-3-phenyl-propionamide;
(S)—N-(4-Aminomethyl-benzyl)-2-{[(R)-3-(4-ethoxy-phenyl)-2-propionylamino-propionyl]-methyl-amino}-3-phenyl-propionamide;
({(R)-1-[(S)-1-(4-Aminomethyl-benzylcarbamoyl)-2-phenyl-ethylcarbamoyl]-2-cyclohexyl-ethyl}-methyl-amino)-acetic acid;
(S)—N-(4-Aminomethyl-3-fluoro-benzyl)-2-{[(R)-3-(4-ethoxy-phenyl)-2-propionylamino-propionyl]-methyl-amino}-3-phenyl-propionamide;
N—[(R)-1-{[(S)-1-(4-Aminomethyl-benzylcarbamoyl)-2-phenyl-ethyl]-methyl-carbamoyl}-2-(4-ethoxy-phenyl)-ethyl]-benzamide;
N—[(R)-1-{[(S)-1-(4-Aminomethyl-benzylcarbamoyl)-2-phenyl-ethyl]-methyl-carbamoyl}-2-(4-ethoxy-phenyl)-ethyl]-isobutyramide;
Naphthalene-1-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;
(R)-2-Amino-N—[(1S,2S)-1-(4-aminomethyl-benzylcarbamoyl)-2-hydroxy-2-phenyl-ethyl]-3-(4-ethoxy-phenyl)-propionamide;
N—[(R)-1-[(S)-1-(4-Aminomethyl-benzylcarbamoyl)-2-phenyl-ethylcarbamoyl]-2-(4-ethoxy-phenyl)-ethyl]-nicotinamide;
(2S,3S)—N-(4-Aminomethyl-benzyl)-2-[(R)-3-(4-ethoxy-phenyl)-2-propionylamino-propionylamino]-3-hydroxy-3-phenyl-propionamide;
N—[(R)-1-[(S)-1-(4-Aminomethyl-benzylcarbamoyl)-2-phenyl-ethylcarbamoyl]-2-(4-ethoxy-phenyl)-ethyl]-isonicotinamide;
Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
Thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
Cyclohexanecarboxylic acid [(R)-1-[(S)-1-(4-aminomethyl-benzylcarbamoyl)-2-phenyl-ethylcarbamoyl]-2-(4-ethoxy-phenyl)-ethyl]-amide;
Isoxazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Pyridine-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Benzo[b]thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

(R)—N—[(S)-1-(4-Aminomethyl-benzylcarbamoyl)-2-phenyl-ethyl]-2-(4-chloro-benzenesulfonylamino)-3-(4-ethoxy-phenyl)-propionamide;

N—[(R)-1-[(S)-1-(4-Aminomethyl-benzylcarbamoyl)-2-phenyl-ethylcarbamoyl]-2-(4-ethoxy-phenyl)-ethyl]-3-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2-chloro-benzamide N—[(R)-1-[(S)-1-(4-Aminomethyl-benzylcarbamoyl)-2-phenyl-ethylcarbamoyl]-2-(4-ethoxy-phenyl)-ethyl]-3-trifluoromethyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide;

(S)—N-(4-Aminomethyl-benzyl)-2-[(R)-3-(4-ethoxy-phenyl)-2-(2-phenylacetylamino-acetylamino)-propionylamino]-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide;

N—[(R)-1-[(S)-1-(4-Aminomethyl-benzylcarbamoyl)-2-phenyl-ethylcarbamoyl]-2-(4-ethoxy-phenyl)-ethyl]-6-methyl-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2-methyl-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2,6-dichloro-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-5,6-dichloro-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2,3,6-trifluoro-isonicotinamide;

N—[(R)-1-[(S)-1-(4-Aminomethyl-benzylcarbamoyl)-2-phenyl-ethylcarbamoyl]-2-(4-ethoxy-phenyl)-ethyl]-3,3,3-trifluoro-propionamide;

2,4-Dimethyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

2-Methyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Chloro-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

4-Methyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

Furan-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Methyl-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-2-methoxy-isonicotinamide;

3-Methyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Amino-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-propoxy-phenyl)-ethyl]-benzamide;

N—[(R)-1-[(S)-1-(4-Aminomethyl-benzylcarbamoyl)-2-pyridin-2-yl-ethylcarbamoyl]-2-(4-ethoxy-phenyl)-ethyl]-benzamide;

N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-(4-chloro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-pyridin-3-yl-ethylcarbamoyl]-2-(4-ethoxy-phenyl)-ethyl]-benzamide;

N—[(R)-1-[(S)-1-(4-Aminomethyl-benzylcarbamoyl)-2-(4-methoxy-phenyl)-ethylcarbamoyl]-2-(4-ethoxy-phenyl)-ethyl]-benzamide;

N—[(R)-1-[(S)-1-(4-Aminomethyl-benzylcarbamoyl)-2-pyridin-4-yl-ethylcarbamoyl]-2-(4-ethoxy-phenyl)-ethyl]-benzamide;

N—[(R)-1-[(S)-1-(4-Aminomethyl-benzylcarbamoyl)-2-(3-fluoro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-thiophen-2-yl-ethylcarbamoyl]-2-(4-ethoxy-phenyl)-ethyl]-benzamide;

N—[(R)-1-[(S)-1-(4-Aminomethyl-benzylcarbamoyl)-2-thiophen-3-yl-ethylcarbamoyl-2-(4-ethoxy-phenyl)-ethyl]-benzamide;

N—[(R)-1-[(S)-1-(4-Aminomethyl-benzylcarbamoyl)-2-thiazol-4-yl-ethylcarbamoyl]-2-(4-ethoxy-phenyl)-ethyl]-benzamide;

N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide;

N—[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide;

N—[(R)-1-[(S)-1-(4-Aminomethyl-3-chloro-benzylcarbamoyl)-2-phenyl-ethylcarbamoyl]-2-(4-ethoxy-phenyl)-ethyl]-benzamide;

Pyridine-2-carboxylic acid [(R)-1-[(S)-1-(4-aminomethyl-benzylcarbamoyl)-2-thiophen-2-yl-ethylcarbamoyl]-2-(4-ethoxy-phenyl)-ethyl]-amide;

N—[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide;

Pyridine-2-carboxylic acid [(R)-1-[(S)-1-(4-aminomethyl-3-chloro-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-isonicotinamide;
Thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-chloro-benzamide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methyl-benzamide;
Pyridine-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;
(R)—N—[(S)-1-(4-Aminomethyl-benzylcarbamoyl)-2-pyridin-2-yl-ethyl]-3-(4-ethoxy-phenyl)-2-propionylamino-propionamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-isonicotinamide;
Pyridine-2-carboxylic acid [(R)-1-[(S)-1-(4-aminomethyl-3-fluoro-benzylcarbamoyl)-2-phenyl-ethylcarbamoyl]-2-(4-ethoxy-phenyl)-ethyl]-amide;
Thiophene-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;
(R)—N—[(S)-1-(4-Aminomethyl-benzylcarbamoyl)-2-pyridin-3-yl-ethyl]-3-(4-ethoxy-phenyl)-2-propionylamino-propionamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-isonicotinamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-3,3,3-trifluoro-propionamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-chloro-benzamide;
Isoxazole-5-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide;
3-Chloro-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide;
3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-(2-fluoro-phenyl)-ethylcarbamoyl]-2-(4-ethoxy-phenyl)-ethyl]-benzamide;
3-Methyl-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-3-methyl-benzylcarbamoyl)-2-phenyl-ethylcarbamoyl]-2-(4-ethoxy-phenyl)-ethyl]-benzamide;
3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;
3-Chloro-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;
N—[(R)-1-[(S)-1-(4-Aminomethyl-benzylcarbamoyl)-2-thiazol-4-yl-ethylcarbamoyl]-2-(4-ethoxy-phenyl)-ethyl]-4-methyl-benzamide;
3-Methyl-1H-pyrrole-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;
3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;
3-Acetylamino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-3-methyl-benzamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-2-methyl-benzamide;
3,5-Dimethyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-3-methyl-benzylcarbamoyl)-2-pyridin-3-yl-ethylcarbamoyl]-2-(4-ethoxy-phenyl)-ethyl]-benzamide;
3-Acetylamino-thiophene-2-carboxylic acid [(R)-1-[(S)-1-(4-aminomethyl-benzylcarbamoyl)-2-thiophen-3-yl-ethylcarbamoyl]-2-(4-ethoxy-phenyl)-ethyl]-amide;
3-Amino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;
3-Acetylamino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;
3-Chloro-thiophene-2-carboxylic acid [(R)-1-{[(S)-1-(4-aminomethyl-benzylcarbamoyl)-2-phenyl-ethyl]-methyl-carbamoyl}-2-(4-ethoxy-phenyl)-ethyl]-amide;
N—[(R)-1-[(1S,2R)-1-(4-Aminomethyl-benzylcarbamoyl)-2-hydroxy-2-phenyl-ethylcarbamoyl]-2-(4-ethoxy-phenyl)-ethyl]-benzamide;
3-Chloro-thiophene-2-carboxylic acid [(R)-1-[(1S,2R)-1-(4-aminomethyl-benzylcarbamoyl)-2-hydroxy-2-phenyl-ethylcarbamoyl]-2-(4-ethoxy-phenyl)-ethyl]-amide;
N—{(R,S)-1-[(S)-1-(4-Aminomethyl-benzylcarbamoyl)-2-phenyl-ethylcarbamoyl]-2-[4-(2,2,2-trifluoro-ethoxy)-phenyl]-ethyl}-benzamide;
or a pharmaceutically acceptable salt or solvate thereof.

9. The process of claim 1, wherein the active ingredient is N—[(R)-1-[(S)-1-(4-aminomethyl-benzylcarbamoyl)-2- phenyl-ethylcarbamoyl]-2-(4-ethoxy-phenyl)-ethyl]-benzamide, or a pharmaceutically acceptable salt or solvate thereof.

10. The process of claim 1, wherein the composition comprises one or more pharmaceutically acceptable excipients.

11. The process of claim 1, wherein the composition comprises a non-ionic surfactant.

12. The process of claim 11, wherein the non-ionic surfactant is polysorbate 80.

13. The process of claim 11, wherein the non-ionic surfactant is polysorbate 20.

14. The process of claim 1, wherein the composition comprises one or more tonicity agents.

15. The process of claim 14, wherein the one or more tonicity agent is trehalose.

16. The process of claim 14, wherein the one or more tonicity agent is dextrose.

17. The process of claim 1, wherein the composition comprises one or more stabilising agents and one or more tonicity agents.

18. The process of claim 17, wherein the one or more stabilising agent is polysorbate 80 or polysorbate 20 and the one or more tonicity agent is dextrose or trehalose.

19. The process of claim 18, wherein the one or more stabilising agent is polysorbate 20 and the one or more tonicity agent is trehalose.

20. The process of claim 18, wherein the one or more stabilising agent is polysorbate 80 and the one or more tonicity agent is dextrose.

21. The process of claim 1, wherein the composition has a pH of from about 2 to about 10.

22. The process of claim 21, wherein the composition has a pH of from about 4 to about 8.

23. The process of claim 1, wherein the composition has an osmolality of from about 250 to about 350 mOsmol/kg.

24. The process of claim 1, wherein the active ingredient is crystalline.

25. The process of claim 1, wherein the active ingredient is amorphous.

26. The process of claim 1, wherein the composition comprises particles of the active ingredient having a particle size distribution with a median value of from about 10 nm to about 100 μm.

27. The process of claim 26, wherein the median value of the particle size distribution is from about 10 nm to about 1000 nm.

28. The process of claim 1, wherein the composition is suitable for intravitreous administration.

29. The process of claim 1, wherein the aqueous pharmaceutical suspension composition is suitable for intraocular parenteral administration.

30. The process of claim 1, wherein the composition comprises one or more stabilising agents.

31. The process of claim 30, wherein the aqueous pharmaceutical suspension comprises one or more stabilizing agents in an amount of less than 0.1 wt %.

32. The process of claim 1, wherein the composition is suitable for intravenous administration.

* * * * *